US012582660B2

(12) United States Patent
Clark et al.

(10) Patent No.: US 12,582,660 B2
(45) Date of Patent: Mar. 24, 2026

(54) INHIBITORS OF THE RAS ONCOPROTEIN, METHODS OF MAKING AND METHODS OF USE THEREOF

(71) Applicant: University of Louisville Research Foundation, Inc., Louisville, KY (US)

(72) Inventors: Geoffrey J. Clark, Pewee Valley, KY (US); John O. Trent, Louisville, KY (US); Joseph A. Burlison, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 17/053,057

(22) PCT Filed: May 10, 2019

(86) PCT No.: PCT/US2019/031885

§ 371 (c)(1),
(2) Date: Nov. 4, 2020

(87) PCT Pub. No.: WO2019/217933

PCT Pub. Date: Nov. 14, 2019

(65) Prior Publication Data

US 2021/0137939 A1 May 13, 2021

Related U.S. Application Data

(60) Provisional application No. 62/669,926, filed on May 10, 2018.

(51) Int. Cl.

| | |
|---|---|
| ***A61K 31/55*** | (2006.01) |
| ***A61K 31/357*** | (2006.01) |
| ***A61K 31/40*** | (2006.01) |
| ***C07K 16/28*** | (2006.01) |

(52) U.S. Cl.

CPC ............ *A61K 31/55* (2013.01); *A61K 31/357* (2013.01); *A61K 31/40* (2013.01); *C07K 16/2818* (2013.01)

(58) Field of Classification Search

CPC .... C07K 16/2818; A61K 31/55; A61K 31/40; A61K 31/357

See application file for complete search history.

(56) References Cited

U.S. PATENT DOCUMENTS 4,944,796 A * 7/1990 Wee .................... C07C 271/22
504/315
2008/0139534 A1 6/2008 Huang et al.
2009/0124620 A1 5/2009 Miyata et al.
2011/0201806 A1 8/2011 Burke et al.
2016/0000812 A1 1/2016 Hartman et al.
2018/0044314 A1 2/2018 Piazza et al.

FOREIGN PATENT DOCUMENTS

CN 101919842 A 12/2010
EP 2759533 7/2014
JP 60233051 11/1985
JP 2011506580 A 3/2011
KR 10-2012-0048223 5/2012
WO 1999/64398 12/1999
WO 2009/080805 7/2009
WO 2009/136175 11/2009
WO WO-2011130628 A1 * 10/2011 ............ A61K 31/38
WO 2012/073041 A2 6/2012
WO 2014/037726 3/2014
WO WO-2014118418 A1 * 8/2014 ............ A61P 35/00
WO 2014/169167 10/2014
WO 2017/161144 9/2017
WO 2019/217933 11/2019

OTHER PUBLICATIONS

Chacon-Garcia et al., "Cytotoxic activity and QSAR of N, N'-diarylalkanediamides" European Journal of Medicinal Chemistry, vol. 36, Issue 9, Jul. 11, 2001, pp. 731-736 (Year: 2001).*
Wang et al., "Gene Essentiality Profiling Reveals Gene Networks and Synthetic Lethal interactions with Oncogenic Ras", Cell, 168, pp. 890-903, Feb. 23, 2017 (Year: 2017).*
American Chemical Society, Chemical Abstract Service, RN: 851459-61-5, First made available to the public Jun. 1, 2005 (Year: 2005).*
American Chemical Society, Chemical Abstract Service, RN: 1004016-25-4, First made available to the public Feb. 17, 2008 (Year: 2008).*
American Chemical Society, Chemical Abstract Service, RN: 1024445-31-5, First made available to the public Jun. 1, 2008 (Year: 2008).*
American Chemical Society, Chemical Abstract Service, RN: 1004631-61-1, First made available to the public Feb. 20, 2008) (Year: 2008).*
First Official Action of Substantial Examination in MX/a/2020/011991 mailed Apr. 26, 2023, 7 pages (with English language translation, 6 pages) (13 pages total).

(Continued)

*Primary Examiner* — Andrew D Kosar
*Assistant Examiner* — Gillian A Hutter
(74) *Attorney, Agent, or Firm* — ALGM LLP; Harry J. Guttman

(57) ABSTRACT

A compound for use in treating a disease associated with activating mutations in RAS, or for use in treating a disease treatable by a reduction in RAS activity, is selected from a compound of Formula (I), salts and esters thereof. The compounds are particularly useful in treating cancer.

(I)

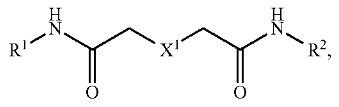

20 Claims, 12 Drawing Sheets

Specification includes a Sequence Listing.

(56) References Cited

OTHER PUBLICATIONS

Hobbs, G.A. et al., "RAS isoforms and mutations in cancer at a glance", Journal of Cell Science, vol. 129, No. 7, pp. 1287-1292, (2016).
American Cancer Society, "Cancer Facts and Figures 2017", pp. 1-76, (2017).
Ostrem, J.M. et al., "K-RAS(G12C) inhibitors allosterically control GTP affinity and effector interactions", Nature, vol. 503, No. 7477, pp. 548-551, (2013).
Shima, F. et al., "In silico discovery of small-molecule RAS inhibitors that display antitumor activity by blocking the RAS-effector interaction", Proceeding of the National Academy of Science, vol. 110, No. 20, pp. 8182-8187, (2013).
Welsch, M.E. et al., "Multivalent small-molecule pan-RAS Inhibitors", Cell, vol. 168, No. 5, pp. 878-889, pp. E1-E23, (2017).
Henry, D.W., "A facile synthesis of piperazines from primary amines", Journal of Heterocyclic Chemistry, vol. 3, issue 4, pp. 503-511, (1966).
Yamaoka, N. et al., "Structure-activity relationships of new N-acylanthranilic acid derivatives as plasminogen activator inhibitor-1 inhibitors", Chemical & Pharmaceutical Bulletin, vol. 59, No. 2, pp. 215-224, (2011).
Kil, K.-E. et al., "Synthesis and evaluation of N-(methylthiophenyl)picolinamide derivatives as PET radioligands for metabotropic glutamate receptor subtype 4", Bioorganic & Medicinal Chemistry Letters, vol. 26, issue 1, pp. 133-139, (2016).
Ledford, H., "The RAS renaissance", Nature, vol. 520, pp. 278-280, (2015).
Colburn, N.H. et al., "Correlation of anchorage-independent growth with tumorigenicity of chemically transformed mouse epidermal cells", Cancer Research, vol. 38, No. 3, pp. 624-634, (1978).
Guidance for Industry: Estimating the Maximum Safe Starting Dose in Initial Clinical Trials for Therapeutics in Adult Healthy Volunteers by U.S. Department of Health and Human Services, Food and Drug Administration, Center for Drug Evaluation and Research CDER, (Jul. 2005).
International Search Report dated Aug. 30, 2019 for PCT application No. PCT/US2019/031885.
Fisher, G.H. et al., "Induction and apoptotic regression of lung adenocarcinomas by regulation of a K-Ras transgene in the presence and absence of tumor suppressor genes", Genes & Development, vol. 15, No. 24, pp. 3249-3262, (2001).
Kohl, N.E. et al., "Inhibition of farnesyltransferase induces regression of mammary and salivary carcinomas in ras transgenic mice", Nature Medicine, vol. 1, No. 8, pp. 792-797, (1995).
Ostrem, J.M.L. et al., "Direct small-molecule inhibitors of KRAS: from structural insights to mechanism-based design", Nature Reviews, vol. 15, pp. 771-785, (2016).
Bos, J.L., "ras Oncogenes in human cancer: A review", Cancer Research, vol. 49, pp. 4682-4689, (1989).
Keeton, A.B. et al., "The RAS-effector interaction as a drug target", Cancer Research, vol. 77, No. 2, pp. 221-226, (2017).
Kaczor, A.A. et al., "Structure-based virtual screening for dopamine $D_2$ receptor ligands as potential antipsychotics", ChemMedChem, vol. 11, pp. 718-729, (2016).
Milton, J. et al., "Biaryl acids: Novel non-nucleoside inhibitors of HIV reverse transcriptase types 1 and 2", Bioorganic & Medicinal Chemistry Letters, vol. 8, pp. 2623-2628, (1998).
European Search Report dated Jan. 19, 2022 for EP application No. EP 19800358.4.
Chacon-Garcia, L. et al., "Cytotoxic activity and QSAR of $N,N^1$-diarylalkanediamides", European Journal of Medicinal Chemistry, vol. 36, issue 9, pp. 731-736, (2001).
7 pages, mailed Aug. 30, 2019, PCT/US2019/031885, WO.
9 pages, mailed Jan. 19, 2022, 19800358.4, EP.
9 pages, mailed Jan. 31, 2022, U.S. Appl. No. 17/053,057, US.
6 pages, mailed Jun. 1, 2022, 202027048402, IN.
11 pages, mailed Aug. 16, 2022, U.S. Appl. No. 17/053,057, US.
5 pages, mailed Sep. 29, 2022, 248596, IL.
24 pages, mailed Nov. 9, 2022, 2020140423, RU.
Official Action in RU 2020140423 mailed Nov. 9, 2022, 14 pages.
Official Action in RU 2020140423 mailed Nov. 9, 2022—English language translation, 13 pages.
Official Action in IL 278596 mailed May 14, 2023, 4 pages.
Official Action in JP 2020-562120 mailed May 22, 2023, 5 pages.
Official Action in JP 2020-562120 mailed May 22, 2023—English language translation, 7 pages.
Official Action in MX MX/a/2020/011991 mailed Oct. 10, 2023, 5 pages.
Official Action in MX MX/a/2020/011991 mailed Oct. 10, 2023—English language translation, 4 pages.
Official Action in JP 2020-562120 mailed Oct. 23, 2023, 3 pages.
Official Action in JP 2020-562120 mailed Oct. 23, 2023—English language translation, 4 pages.
Official Action in CN 201980038063.7 mailed Oct. 25, 2023, 5 pages.
Official Action in CN 201980038063.7 mailed Oct. 25, 2023—English language translation, 8 pages.
Official Action in RU 2020140423 mailed Jan. 25, 2024, 6 pages.
Official Action in RU 2020140423 mailed Jan. 25, 2024—English language translation, 6 pages.
Official Action in IL 278596 mailed Feb. 21, 2024, 3 pages.
Official Action in AU 2019265011 mailed Mar. 13, 2024, 4 pages.
Belikov, "Pharmaceutical Chemistry", Chapter 2.6 "Relationship between the chemical structure, properties of substances and their effect on the body", MEDpressinform, Moscow, 2007, pp. 27-29.
Belikov, "Pharmaceutical Chemistry", Chapter 2.6 "Relationship between the chemical structure, properties of substances and their effect on the body", MEDpressinform, Moscow, 2007, pp. 27-29. (Google Machine English translation) (16 pages).
CAS Registry cited compounds (indicated entries from 2005 to 2008)—Found searching STN online (Search date: May 11, 2023): CAS Registration Nos. 1024445-31-5, 1004631-61-1, 1004016-25-4, 851459-61-5. (4 pages).
Hill et al. (1920) "Researches on Amines. VIII. Preparation of amino-acetanilide" Journal of the American Chemical Society, vol. 42, pp. 1704-1711.
Kubicova et al. (2000) "Synthesis of N, N'-Diarylalkanediamides and Their Antimycobacterial and Antialgal Activity" Molecules, vol. 5, pp. 714-726.
CN101919842A English-language abstract from Espacenet, 2010 (1 page).

* cited by examiner

| Cancer | Isoform | Percentage |
| --- | --- | --- |
| Pancreatic ductal adenocarcinoma | K | 98 |
| Colorectal adenocarcinoma | K | 52 |
| Multiple myeloma | K, N | 43 |
| Lung adenocarcinoma | K | 32 |
| Skin cutaneous melanoma | N | 29 |
| Uterine corpus endometrioidcarcinoma | K | 25 |
| Uterine carcinosarcoma | K | 14 |
| Thyroid carcinoma | N>H | 13 |
| Acute myeloid leukemia | N>K>H | 11 |
| Bladder urothelial carcinoma | H,K>N | 11 |
| Gastric adenocarcinoma | K | 10 |
| Cervical adenocarcinoma | K | 8 |
| Head and neck squamous cell carcinoma | H | 6 |

FIG. 1

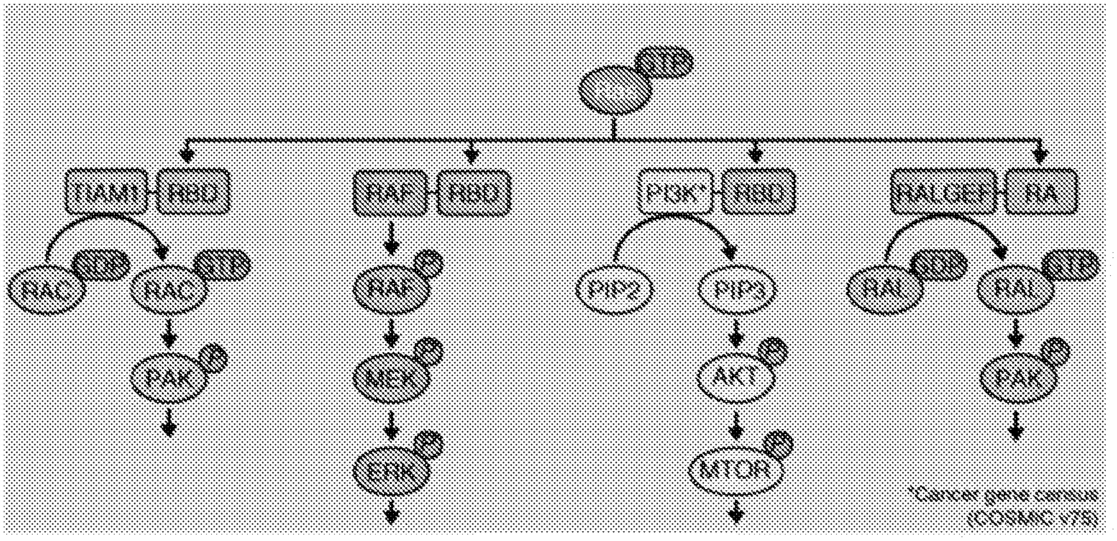

FIG. 2A

SEQUENCE LISTING

```
<160> NUMBER OF SEQ ID NOS: 2

<210> SEQ ID NO 1
<211> LENGTH: 167
<212> TYPE: PRT
<213> ORGANISM: Homo sapiens

<400> SEQUENCE: 1

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Lys Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys
                165


<210> SEQ ID NO 2
<211> LENGTH: 188
<212> TYPE: PRT
<213> ORGANISM: Homo sapiens

<400> SEQUENCE: 2

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
```

-continued

```
              85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

INHIBITORS OF THE RAS ONCOPROTEIN, METHODS OF MAKING AND METHODS OF USE THEREOF

GOVERNMENT RIGHTS

This invention was made with the following U.S. Government support: (a) grant numbers RR018733, HL127518, GM103482, and GM106396 funded by the National Institutes of Health (NIH) and (b) grant number W81XWH-19-1-0417 funded by the Defense Health Agency Research and Development Program (DHA/MRDB). The U.S. Government has certain rights in this invention.

REFERENCE TO A SEQUENCE LISTING

The instant application contains a Sequence Listing that has been submitted in ASCII format via PatentCenter and is hereby incorporated by reference in its entirety. Said ASCII copy, created on Nov. 9, 2025, is named "17036 04 4173-2025 11_ST25.txt" and is 4,096 B in size.

BACKGROUND

RAS is the most common oncogene in human cancer. Activating mutations in one of the 3 human RAS gene isoforms (KRAS, HRAS, or NRAS) are present in about one-fourth of all cancers [1]. KRAS is also found in two alternatively spliced forms, referred to as KRAS4A and KRAS4B. For example, mutant KRAS is found in 98% of pancreatic ductal adenocarcinomas, 52% of colon cancers, and 32% of lung adenocarcinomas (FIG. 1 and [1]). Just for these three cancer types alone, that means that cancers with mutant KRAS are diagnosed in more than 170,000 people each year in the US and cause more than 120,000 deaths [2]. There are no FDA-approved direct RAS protein inhibitors currently available. Drugs that target signaling downstream of RAS are available but have shown disappointing clinical activity, most likely because RAS is a "hub" that activates multiple effectors (FIG. 2A) and blocking any single pathway (or even two) would be ineffective.

RAS is a G-protein that works as a switch, toggling between "on" and "off" when bound to guanosine nucleotides, GTP or GDP. The RAS mutations found in cancer cause the protein to be turned on (that is, bound to GTP) most of the time [1]. Most drug targets are proteins that have a well-defined "pocket" that can be targeted by small molecules, as with enzymes (substrate binding site) or kinases (ATP binding site). RAS lacks such pockets and thus is more difficult to target directly.

RAS inhibitors are known, but none have resulted in an approved treatment. An inhibitor of a single specific KRAS mutation, KRAS(G12C), is known, which was capable of inhibiting one tumor cell line with the G12C mutation and resulted in 30% apoptosis at a concentration of 1-10 μM [3]. Furthermore, two small-molecule RAS inhibitors, referred to Kobe0065 and Kobe2602, effectively inhibited anchorage-dependent and -independent growth of HRAS transformed NIH 3T3 cells, showing an IC50 at a concentration of 2-10 μM [4]. More recently, a small molecule pan-RAS, showing effectiveness in an in vivo xenograft mouse cancer models was identified [5].

SUMMARY

A compound for use in treating a disease associated with activating mutations in RAS, or for use in treating a disease treatable by a reduction in RAS activity, is selected from a compound of Formula (I),

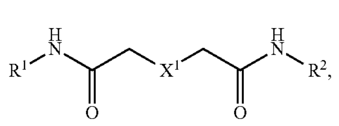

(I)

and salts and esters thereof. The compounds are particularly useful in treating cancer.

DEFINITIONS

As used herein (unless otherwise specified), the term "alkyl" means a monovalent, straight or branched hydrocarbon chain. For example, the terms "$C_1$-$C_7$ alkyl" or "$C_1$-$C_4$ alkyl" refer to straight- or branched-chain saturated hydrocarbon groups having from 1 to 7 (e.g., 1, 2, 3, 4, 5, 6, or 7), or 1 to 4 (e.g., 1, 2, 3, or 4), carbon atoms, respectively. Examples of $C_1$-$C_7$ alkyl groups include, but are not limited to, methyl, ethyl, n-propyl, i-propyl, n-butyl, s-butyl, t-butyl, n-pentyl, s-pentyl, n-hexyl, and n-septyl. Examples of $C_1$-$C_4$ alkyl groups include, but are not limited to, methyl, ethyl, n-propyl, i-propyl, n-butyl, s-butyl, and t-butyl.

As used herein (unless otherwise specified), the term "alkenyl" means a monovalent, straight or branched hydrocarbon chain that includes one or more (e.g., 1, 2, 3, or 4) double bonds. Examples of alkenyl groups include, but are not limited to, vinyl, allyl, 1-propenyl, 2-propenyl, 1-butenyl, 2-butenyl, 3-butenyl 1-pentenyl, 2-pentenyl, 3-pentenyl, 4-pentenyl, 1-hexenyl, 2-hexenyl, 3-hexenyl, 4-hexenyl, and 5-hexenyl.

As used herein (unless otherwise specified), the term "alkoxy" means any of the above alkyl groups which is attached to the remainder of the molecule by an oxygen atom (alkyl-O—). Examples of alkoxy groups include, but are not limited to, methoxy (sometimes shown as MeO—), ethoxy, isopropoxy, propoxy, and butyloxy.

As used herein (unless otherwise specified), the term "alkynyl" means a monovalent, straight or branched hydrocarbon chain that includes one or more (e.g., 1, 2, 3, or 4) triple bonds and that also may optionally include one or more (e.g. 1, 2, 3, or 4) double bonds in the chain. Examples of alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

As used herein (unless otherwise specified), the term "aryl" means a monovalent, monocyclic or bicyclic, 5, 6, 7, 8, 9, 10, 11, or 12 member aromatic hydrocarbon group which, when unsubstituted. Examples of aryl groups include, but are not limited to, phenyl, naphthyl, tolyl, and xylyl. For an aryl that is bicyclic, one or both rings can be substituted.

As used herein (unless otherwise specified), the term "cycloalkyl" means a monovalent, monocyclic or bicyclic, 3, 4, 5, 6, 7, 8, 9, 10, 11, or 12 membered hydrocarbon group. The rings can be saturated or partially unsaturated. Examples of cycloalkyl groups include, but are not limited to, cyclopropyl, cyclobutyl, cyclopentyl, cyclohexyl, cycloheptyl, cyclooctyl, and bicycloalkyls (e.g., bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds). For a monocyclic cycloalkyl, the ring is not aromatic. For a bicyclic cycloalkyl, if one ring is aromatic, then the other is not aromatic. For a bicyclic cycloalkyl, one or both rings can be substituted.

As used herein (unless otherwise specified), the term "halogen" means monovalent Cl, F, Br, or I.

As used herein (unless otherwise specified), the term "heteroaryl" means a monovalent, monocyclic or bicyclic, 5, 6, 7, 8, 9, 10, 11, or 12 membered, hydrocarbon group, where 1, 2, 3, 4, 5, or 6 carbon atoms are replaced by a hetero atom independently selected from nitrogen, oxygen, or sulfur atom, and the monocyclic or bicyclic ring system is aromatic. Examples of heteroaryl groups include, but are not limited to, thienyl (or thiophenyl), furyl, indolyl, pyrrolyl, pyridinyl, pyrazinyl, oxazolyl, thiaxolyl, quinolinyl, pyrimidinyl, imidazolyl, 1-methyl-imidazolyl, triazolyl, tetrazolyl, H-pyrazol-4-yl, 1-Me-pyrazol-4-yl, pyridin-3-yl, pyridin-4-yl, 3,5-dimethylisoxazolyl, 1H-pyrrol-3-yl, 3,5-di-Me-pyrazolyl, and 1H-pyrazol-4-yl. For a bicyclic heteroaryl, if one ring is aryl, then the other is heteroaryl. For a bicyclic heteroaryl, one or both rings can have one or more hetero atoms. For a bicyclic heteroaryl one or both rings can be substituted. An N-heteroaryl means a heteroaryl that comprises one or more N atoms (e.g., 1, 2, 3, 4, 5, or 6); an N-heteroaryl may also comprise other hetero atoms. An O-heteroaryl means a heteroaryl that comprises one or more 0 atoms (e.g., 1, 2, 3, 4, 5, or 6); an O-heteroaryl may also comprise other hetero atoms. An S-heteroaryl means a heteroaryl that comprises one or more S atoms (e.g., 1, 2, 3, 4, 5, or 6); an S-heteroaryl may also comprise other hetero atoms.

As used herein (unless otherwise specified), the term "heterocyclyl" means a monovalent, monocyclic or bicyclic, 5, 6, 7, 8, 9, 10, 11, or 12 membered, hydrocarbon, where 1, 2, 3, 4, 5, or 6 carbon atoms are replaced by a hetero atom independently selected from nitrogen atom, oxygen atom, or sulfur atom, and the monocyclic or bicyclic ring system is not aromatic. Examples of heterocyclyl groups include, but are not limited to, benzodioxolyl, tetrahydropyranyl, pyrrolidinyl (e.g., pyrrolidin-1-yl, pyrrolidin-2-yl, pyrrolidin-3-yl or pyrrolidin-4-yl), piperazinyl (e.g., piperazin-1-yl, piperazin-2-yl, piperazin-3-yl, or piperazin-4-yl), piperidinyl (e.g., piperadin-1-yl, piperadin-2-yl, piperadin-3-yl, or piperadin-4-yl), azepanyl (e.g., azepan-1-yl, azepan-2-yl, azepan-3-yl, azepan-4-yl or azepan-5-yl), azocanyl (e.g., azocan-1-yl azocan-2-yl, azocan-3-yl, azocan-4-yl, azocan-5-yl azocan-6-yl, or azocan-7-yl), azonanyl (e.g., 1-azonanyl), and morpholinyl (e.g., morpholin-1-yl, morpholin-2-yl, morpholin-3-yl, or morpholin-4-yl). For a bicyclic heterocyclyl, if one ring is aromatic (e.g., monocyclic aryl or heteroaryl), then the other ring is not aromatic. For a bicyclic heterocyclyl, one or both rings can have one or more hetero atoms. For a bicyclic heterocyclyl one or both rings can be substituted. An N-heterocyclyl means a heterocycyl, that comprises one or more N atoms (e.g., 1, 2, 3, 4, 5, or 6); an N-heterocyclyl may also comprise other hetero atoms. An O-heterocyclyl means a heterocycyl, that comprises one or more 0 atoms (e.g. 1, 2, 3, 4, 5, or 6); an O-heterocyclyl may also comprise other hetero atoms. An S-heterocyclyl means a heterocyclyl, that comprises one or more S atoms (e.g., 1, 2, 3, 4, 5, or 6); an S-heterocyclyl may also comprise other hetero atoms.

As used herein (unless otherwise specified), the term "hetero atom" means an atom selected from nitrogen atom, oxygen atom, or sulfur atom.

As used herein (unless otherwise specified), the terms "hydroxy" or "hydroxyl" indicates the presence of a monovalent —OH group.

As used herein (unless otherwise specified), the term "substituted" (e.g., as in substituted alkyl) means that one or more hydrogen atoms of a chemical group (with one or more hydrogen atoms) can be replaced by one or more non-hydrogen substituents selected from the specified options. The replacement can occur at one or more positions. The term "optionally substituted" means that one or more hydrogen atoms of a chemical group (with one or more hydrogen atoms) can be, but is not required to be substituted.

Some compounds of the invention can have one or more chiral centers and can exist in and be isolated in optically active and racemic forms, for any of the one or more chiral centers. Some compounds can exhibit polymorphism. The compounds of the present invention encompass any optically active, racemate, or mixtures thereof, if a chiral center does not provide an indication of its configuration (i.e., R or S) in a chemical structure, it should be considered to represent R, S or a racemate. When structural formulas are presented without specifying chirality of chiral centers, it should be considered to represent R, S or a racemate.

Unless otherwise specified, all carbon containing groups may contain 1 to 20 carbon atoms.

Tumors and cancers include solid, dysproliferative tissue changes and diffuse tumors. Examples of tumors and cancers include melanoma, lymphoma, plasmocytoma, sarcoma, glioma, thymoma, leukemia, breast cancer, prostate cancer, colon cancer, liver cancer, esophageal cancer, brain cancer, lung cancer, ovary cancer, endometrial cancer, bladder cancer, kidney cancer, cervical cancer, hepatoma, and other neoplasms. For more examples of tumors and cancers, see, for example Stedman [13].

"Treating a tumor" or "treating a cancer" means to significantly inhibit growth and/or metastasis of the tumor or cancer. Growth inhibition can be indicated by reduced tumor volume or reduced occurrences of metastasis. Tumor growth can be determined, for example, by examining the tumor volume via routine procedures (such as obtaining two-dimensional measurements with a dial caliper). Metastasis can be determined by inspecting for tumor cells in secondary sites or examining the metastatic potential of biopsied tumor cells in vitro.

A "chemotherapeutic agent" is a chemical compound that can be used effectively to treat cancer in humans.

A "pharmaceutically acceptable carrier" includes any and all solvents, dispersion media, coatings, antibacterial and antifungal agents, isotonic and absorption delaying agents which are compatible with pharmaceutical administration. Preferred examples of such carriers or diluents include water, saline, Ringer's solutions and dextrose solution, as well as solid excipients. Supplementary active compounds can also be incorporated into the compositions.

"Medicament," "therapeutic composition" and "pharmaceutical composition" are used interchangeably to indicate a compound, matter, mixture or preparation that exerts a therapeutic effect in a subject.

As used herein, RAS refers to all forms of the gene, including KRAS, HRAS, NRAS, while KRAS refers to both KRAS4A and KRAS4B.

BRIEF DESCRIPTION OF THE DRAWINGS

FIG. 1 is a chart of the prevalence of mutant KRAS in different types of cancers.

FIG. 2A is an illustration of RAS as a "hub" that activates multiple effectors.

DETAILED DESCRIPTION

Figure 2B:
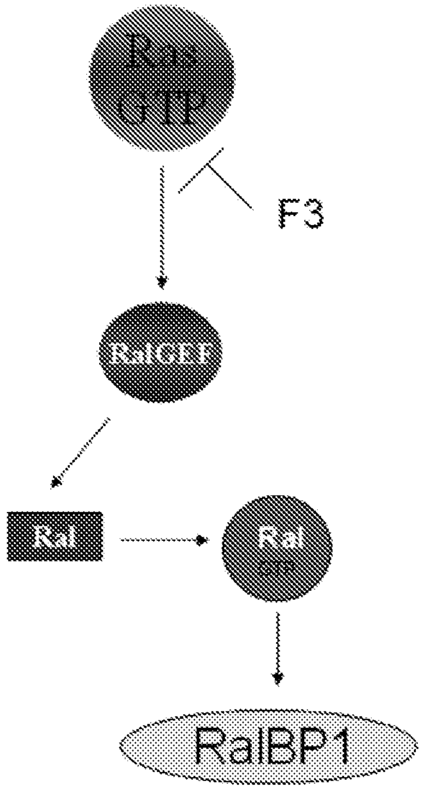
FIG. 2B illustrates the pathway by which RAS binds RalGDS proteins.

The present application is based on the development of small molecules that are protein-protein interaction (PPI) inhibitors that block the binding of RAS to its effector proteins. An in silico examination of a library of over one million compounds identified many potential inhibitors. The top ranked potential inhibitors were obtained and tested, to identify lead compounds. Variations of the lead compounds were prepared and tested, both in vitro and in vivo, and this has resulted in the identification of large family of RAS inhibitors.

Because the HRAS structure in complex with RALGDS was known, this form of RAS was used for the in silico examination. However, testing of the compounds for activity was against the much more important K-RAS isoform. In any event, much of the sequence between different forms is highly conserved and the differences between the different forms of RAS is located in a region which is not believe to have much effect on binding, therefore the effect of the compounds on inhibition of RAS is not expected to vary significantly between the different forms.

The compounds identified bind directly to RAS and blocks its effector interactions and signaling activity. They block the transforming activity of RAS without suppressing normal cellular growth and survival. Furthermore, they may act via anoikis (at least in part) and suppresses tumor formation in vivo.

```
H-RAS reference sequence:
                                              (SEQ ID NO: 1)
MTEYKLVVVGAGGVGKSALTIQLIQNHFVDKYDPTIEDSYRKQVVIDGET

CLLDILDTAGQEEYSAMRDQYMRTGEGFLCVFAINNTKSFEDIHQYREQI

KRVKDSDDVPMVLVGNKCDLAARTVESRQAQDLARSYGIPYIETSAKTRQ

GVEDAFYTLVREIRQHK.

K-RAS4B reference sequence:
                                              (SEQ ID NO: 2)
MTEYKLVVVG AGGVGKSALT IQLIQNHFVD EYDPTIEDSY

RKQVVIDGET CLLDILDTAG QEEYSAMRDQ YMRTGEGFLC

VFAINNTKSF EDIHHYREQI KRVKDSEDVP MVLVGNKCDL

PSRTVDTKQA QDLARSYGIP FIETSAKTRQ GVDDAFYTLV

REIRKHKEKM SKDGKKKKKK SKTKCVIM.
```

The target region of RAS reference sequence in contact with RalGEF, its binding partner: ILE 21, ILE 24, GLN 25, HIS 27, VAL 29, LYS 31, ASP 33, PRO 34, THR 35, ILE 36, GLU 37, ASP 38, SER 39, TYR 40, ARG 41, LYS 42, LEU 56, TYR 64, MET 67.

The pocket and residues of the RAS reference sequence for other target region: GLY 13, GLY 15, LYS 16, SER 17, ALA 18, LEU 19, ILE 21, GLN 22, HIS 27, PHE 28, VAL 29, ASP 30, LYS 31, TYR 32, ASP 33, PRO 34, THR 35, ASP 38, TYR 40, ASP 57, ALA 146.

FIG. 28 illustrates the pathway by which RAS binds RalGDS proteins and activates them. In the illustration, F3 represents a RAS inhibitor blocking the binding of RAS to is effector proteins.

RAS inhibitors are any compound selected from a compound of Formula (I),

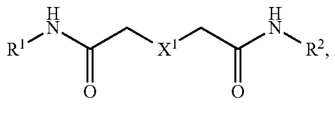

(I)

including optical isomers, as well as salts and esters thereof. $R^1$, $R^2$ and $X^1$ have the following meanings:

$R^1$ is a monovalent H, carboxy (—$CO_2H$), nitro (—$NO_2$), sulfo (—$SO_3H$), halogen (e.g., F, Cl, Br, or I), aryl (e.g., phenyl), cycloalkyl, heterocyclyl, heteroaryl (e.g., pyridinyl), —($C_1$-$C_3$)alkyl-aryl (e.g., -methyl-phenyl), —($C_1$-$C_3$)alkyl-cycloalkyl, —($C_1$-$C_3$)alkyl-heterocyclyl, —($C_1$-$C_3$)alkyl-heteroaryl, $C_1$-$C_8$ alkyl (e.g., $C_1$, $C_2$, $C_3$, $C_4$, $C_5$, $C_6$, $C_7$, or $C_8$ alkyl), $C_2$-$C_8$ alkenyl (e.g., $C_2$, $C_3$, $C_4$, $C_5$, $C_6$, $C_7$, or Ca alkenyl), $C_2$-$C_8$ alkynyl (e.g., $C_2$, $C_3$, $C_4$, $C_5$, $C_7$, or $C_8$ alkynyl), or $C_1$-$C_7$ alkoxy ($C_1$, $C_2$, $C_3$, $C_4$, $C_5$, $C_6$, or $C_7$ alkoxy), which aryl (e.g., phenyl), cycloalkyl, heterocyclyl, heteroaryl (e.g., pyridinyl), —($C_1$-$C_3$)alkyl-aryl (e.g., -methyl-phenyl), —($C_1$-$C_3$)alkyl-cycloalkyl, —($C_1$-$C_3$)alkyl-heterocyclyl, —($C_1$-$C_3$)alkyl-heteroaryl, $C_1$-$C_7$ alkyl, $C_2$-$C_7$ alkenyl, $C_2$-$C_7$ alkynyl, or $C_1$-$C_6$ alkoxy may optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—$CO_2$H), nitro (—$NO_2$), cyano (—CN), amino (—$NH_2$), carbamoyl (—$CONH_2$), ethynyl (—CCH), —$CF_3$, —$CF_2CF_3$, —$OCF_3$, —$OCF_2CF_3$, or sulfo (—$SO_3$H).

$X^1$ is bivalent —(NH)—, —($CH_2$)—, —($NHCH_2$)—, —($CH_2$NH)—, —($C_2H_4$)—, —($C_2H_2$)—, —($C_2$)—, —O—, —O—($CH_2$)—, —($CH_2$)—O—, —S—, —S—($CH_2$)—, or —($CH_2$)—S—, which —(NH)—, —($CH_2$)—, —($NHCH_2$)—, —($CH_2$NH)—, —($C_2H_4$)—, —($C_2H_2$)—, —O—($CH_2$)—, —($CH_2$)—O—, —S—($CH_2$)—, or —($CH_2$)—S— may optionally be substituted with one or more (e.g., 0, 1, 2, 3, or 4) of halogen (e.g., F, Cl, Br, or I), hydroxy (—OH), —$R_x$, methanoly (—COH), carboxy (—$CO_2$H), nitro (—$NO_2$), cyano (—CN), amino (—$NH_2$), carbamoyl (—$CONH_2$), ethynyl (—CCH), —$CF_3$, —$CF_2CF_3$, —$OCF_3$, —$OCF_2CF_3$, or sulfo (—$SO_3$H).

$R_x$ is $C_1$-$C_8$ alkyl (e.g., $C_1$, $C_2$, $C_3$, $C_4$, $C_5$, $C_6$, $C_7$, or $C_7$ alkyl), $C_2$-$C_8$ alkenyl (e.g., $C_2$, $C_3$, $C_4$, $C_5$, $C_6$, $C_7$, or $C_8$ alkenyl), $C_2$-$C_8$ alkynyl (e.g., $C_2$, $C_3$, $C_4$, $C_5$, $C_6$, $C_7$, or $C_8$ alkynyl), or $C_1$-$C_7$ alkoxy ($C_1$, $C_2$, $C_3$, $C_4$, $C_5$, $C_6$, or $C_7$ alkoxy), which $C_1$-$C_8$ alkyl (e.g., $C_1$, $C_2$, $C_3$, $C_4$, $C_5$, $C_6$, $C_7$, or $C_8$ alkyl), $C_2$-$C_8$ alkenyl (e.g., $C_2$, $C_3$, $C_4$, $C_5$, $C_6$, $C_7$, or $C_8$ alkenyl), $C_2$-$C_8$ alkynyl (e.g., $C_2$, $C_3$, $C_4$, $C_5$, $C_6$, $C_7$, or $C_8$ alkynyl), or $C_1$-$C_7$ alkoxy ($C_1$, $C_2$, $C_3$, $C_4$, $C_5$, $C_6$, or $C_7$ alkoxy) may optionally be substituted with one or more (e.g., 0, 1, 2, 3, or 4) of halogen (e.g., F, Cl, Br, or I), hydroxy (—OH), $C_1$-$C_4$ alkyl (e.g., $C_1$, $C_2$, $C_3$, or $C_4$ alkyl), $C_2$-$C_4$ alkenyl (e.g., $C_2$, $C_3$, or $C_4$ alkenyl), $C_2$-$C_4$ alkynyl (e.g., $C_2$, $C_3$, or $C_4$ alkynyl), $C_1$-$C_4$ alkoxy ($C_1$, $C_2$, $C_3$, or $C_4$ alkoxy), aryl, cycloalkyl, heterocyclyl, heteroaryl, methanoly (—COH), carboxy (—$CO_2$H), nitro (—$NO_2$), cyano (—CN), amino (—$NH_2$), carbamoyl (—$CONH_2$), ethynyl (—CCH), —$CF_3$, —$CF_2CF_3$, —$OCF_3$, —$OCF_2CF_3$, or sulfo (—$SO_3$H).

$R^2$ is aryl (e.g., phenyl), cycloalkyl, heterocyclyl (e.g., benzodioxolyl), heteroaryl (e.g., pyridinyl), —($C_1$-$C_3$)alkyl-aryl (e.g., -methyl-phenyl), —($C_1$-$C_3$)alkyl-cycloalkyl, —($C_1$-$C_3$)alkyl-heterocyclyl (e.g., -methyl-benzodioxolyl), or —($C_1$-$C_3$)alkyl-heteroaryl, which aryl, cycloalkyl, heterocyclyl, heteroaryl (e.g., pyridinyl), —($C_1$-$C_3$)alkyl-aryl (e.g., -methyl-phenyl), —($C_1$-$C_3$)alkyl-cycloalkyl, —($C_1$-$C_3$)alkyl-heterocyclyl (e.g., -methyl-benzodioxolyl), or —($C_1$-$C_3$)alkyl-heteroaryl, may optionally be substituted with one or more (e.g., 0, 1, 2, 3, 4, 5, or 6) of halogen (e.g., F, Cl, Br, or I), hydroxy (—OH), $C_1$-$C_{16}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$ alkyl), $C_2$-$C_{16}$ alkenyl (e.g., $C_2$, $C_3$, $C_4$, $C_5$, $C_6$, $C_7$, $C_8$, $CO_9$, $C_{10}$, $C_{11}$, $C_{12}$, $C_{13}$, $C_{14}$, $C_{15}$, or $C_{16}$ alkenyl), $C_2$-$C_{16}$ alkynyl (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$ alkynyl), $C_1$-$C_{15}$ alkoxy ($C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, or $C_{15}$ alkoxy), methanoly (—COH), carboxy (—$CO_2$H), nitro (—$NO_2$), cyano (—CN), amino (—$NH_2$), carbamoyl (—$CONH_2$), ethynyl (—CCH), —$CF_3$, —$CF_2CF_3$, —$OCF_3$, —$OCF_2CF_3$, sulfo (—$SO_3$H), —$SO_2$—$R^3$, —(C═O)—$R_3$, or —O—$R^3$.

$R^3$ is —$NR_aR_b$, aryl, cycloalkyl (e.g., cycloheptyl), heterocyclyl (e.g., 1-azepanyl), heteroaryl (e.g., pyridinyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_2$-$C_7$ alkoxy ($C_1$, $C_2$, $C_3$, $C_4$, $C_5$, or $C_6$ alkoxy), which aryl, cycloalkyl (e.g., cycloheptyl), heterocyclyl (e.g., 1-azepanyl), heteroaryl (e.g., pyridinyl), $C_1$-$C_7$ alkyl, $C_2$-$C_7$ alkenyl, $C_2$-$C_7$ alkynyl, or $C_1$-$C_6$ alkoxy may optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—$CO_2$H), nitro (—$NO_2$), cyano (—CN), amino (—$NH_2$), carbamoyl (—$CONH_2$), ethynyl (—CCH), —$CF_3$, —$CF_2CF_3$, —$CF_3$, —$OCF_2CF_3$, or sulfo (—$SO_3$H).

$R_a$ is monovalent H, aryl (e.g., phenyl), cycloalkyl (e.g., cyclohexyl), heterocyclyl, heteroaryl (e.g., pyridinyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which H, aryl, cycloalkyl, heterocyclyl, heteroaryl (e.g., pyridinyl and 1-methyl imidazolyl), $C_1$-$C_7$ alkyl, $C_2$-$C_7$ alkenyl, $C_2$-$C_7$ alkynyl, or $C_1$-$C_6$ alkoxy may optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—$CO_2$H), nitro (—$NO_2$), cyano (—CN), amino (—$NH_2$), carbamoyl (—$CONH_2$), ethynyl (—CCH), —$CF_3$, —$CF_2CF_3$, —$OCF_3$, —$OCF_2CF_3$, or sulfo (—$SO_3$H).

$R_b$ is monovalent H, aryl (e.g., phenyl), cycloalkyl (e.g., cyclohexyl), heterocyclyl, heteroaryl (e.g., pyridinyl), $C_1$-$C_7$ alkyl (e.g., $C_1$, $C_2$, $C_3$, $C_4$, $C_5$, $C_6$, or $C_7$ alkyl), $C_2$-$C_7$ alkenyl (e.g., $C_2$, $C_3$, $C_4$, $C_5$, $C_6$, or $C_7$ alkenyl), $C_2$-$C_7$ alkynyl (e.g., $C_2$, $C_3$, $C_4$, $C_5$, $C_6$, or $C_7$ alkynyl), or $C_1$-$C_6$ alkoxy ($C_1$, $C_2$, $C_3$, $C_4$, $C_5$, or $C_6$ alkoxy), which H, aryl, cycloalkyl, heterocyclyl, heteroaryl (e.g., pyridinyl and 1-methyl imidazolyl), $C_1$-$C_7$ alkyl, $C_2$-$C_7$ alkenyl, $C_2$-$C_7$ alkynyl, or $C_1$-$C_6$ alkoxy may optionally be substituted with one or more (e.g., 0, 1, 2, 3, 4, 5, or 6) of halogen (e.g., F, Cl, Br, or I), hydroxy (—OH), $C_1$-$C_5$ alkyl (e.g., $C_1$, $C_2$, $C_3$, $C_4$, or $C_5$ alkyl), $C_1$-$C_4$ alkoxy ($C_1$, $C_2$, $C_3$, or $C_4$ alkoxy), methanoly (—COH), carboxy (—$CO_2$H), nitro (—$NO_2$), cyano (—CN), amino (—$NH_2$), carbamoyl (—$CONH_2$), ethynyl (—CCH), —$CF_3$, —$CF_2CF_3$, —$OCF_3$, —$OCF_2CF_3$, or sulfo (—$SO_3$H).

If $R^2$ comprises substitution with one or more of methanoly (—COH), carboxy (—$CO_2$H), amino (—$NH_2$), $C_1$-$C_{16}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$ alkyl), $C_2$-$C_{16}$ alkenyl (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$ alkenyl), $C_2$-$C_{16}$ alkynyl (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$ alkynyl), $C_1$-$C_{15}$ alkoxy ($C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, or $C_{15}$ alkoxy), then each of methanoly (—COH), carboxy (—$CO_2$H), amino (—$NH_2$), $C_1$-$C_{15}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$ alkyl), $C_2$-$C_{16}$ alkenyl (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$ alkenyl), $C_2$-$C_{16}$ alkynyl (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$ alkynyl), $C_1$-$C_{15}$ alkoxy ($C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, or $C_{15}$ alkoxy), may be independently and optionally substituted with one or more (e.g., 0, 1, 2, 3, 4, 5, or 6) of halogen (e.g., F, Cl, Br, or I), hydroxy (—OH), $C_1$-$C_4$ alkyl (e.g., $C_1$, $C_2$, $C_3$, or $C_4$ alkyl), $C_2$-$C_4$ alkenyl (e.g., $C_2$, $C_3$, or $C_4$ alkenyl), $C_2$-$C_4$ alkynyl (e.g., $C_2$, $C_3$, or $C_4$ alkynyl), $C_1$-$C_4$ alkoxy ($C_1$, $C_2$, $C_3$, or $C_4$ alkoxy), methanoly (—COH), carboxy (—$CO_2$H), nitro (—$NO_2$), cyano (—CN), amino (—$NH_2$), —NH($C_1$-$C_4$ alkyl) (e.g., —$NHCH_2CH_3$), —N($C_1$-$C_4$ alkyl)($C_1$-$C_4$ alkyl)

(e.g., —$N(CH_3)_2$), carbamoyl (—$CONH_2$), ethynyl (—CCH), —$CF_3$, —$CF_2CF_3$, —$OCF_3$, —$OCF_2CF_3$, sulfo (—$SO_3H$), or —$R_c$.

$R_c$ may be the same or different for each choice, and may be —CO—$OCH_3$ (methyl carboxy), —CO—$NR_fR_g$, —$SO_2$—$NR_fR_g$, —$NR_fR_g$, —NH—CO—$CH_3$, —NH—CO—$NR_fR_g$, —NH—CO—$OCH_3$, aryl, cycloalkyl, heterocyclyl, heteroaryl, 5-7 membered monocyclic heterocyclyl, 5-7 membered monocyclic heteroaryl, tetrazolyl (e.g., 5-tetrazolyl, 2-tetrazolyl, or 1-tetrazolyl), triazolyl (e.g., 1-triazolyl, 2-triazolyl, or 4-triazolyl), imidazolyl (e.g., 1-imidazolyl), pyrrolyl (e.g., 1-pyrrolyl), pyrrolidinyl (e.g., 1-pyrrolidinyl), piperidyl (e.g., 1-piperidyl), piperazinyl (e.g., 1-piperazinyl), morpholinyl (e.g., 4-morpholinyl), pyridyl (e.g., 2-pyridyl), pyrazinyl (e.g., 2-pyrazinyl), pyrimidinyl (e.g., 4-pyrimidinyl), thienyl, furyl, pyranyl, pyrazolyl, isothiazolyl isoxazolyl, pyridazinyl, furazanyl, pyrrolinyl, imidazolidinyl, imidazolinyl, pyrazolidinyl, or pyrazolinyl, which —CO—$OCH_3$ (methyl carboxy), —CO—$NR_fR_g$, —$SO_2$—$NR_fR_g$, —$NR_fR_g$, —NH—CO—$CH_3$, —NH—CO—$NR_fR_g$, —NH—CO—$OCH_3$, aryl, cycloalkyl, heterocyclyl, heteroaryl, 5-7 membered monocyclic heterocyclyl, 5-7 membered monocyclic heteroaryl, tetrazolyl (e.g., 5-tetrazolyl, 2-tetrazolyl, or 1-tetrazolyl), triazolyl (e.g., 1-triazolyl, 2-triazolyl, or 4-triazolyl), imidazolyl (e.g., 1-imidazolyl), pyrrolyl (e.g., 1-pyrrolyl), pyrrolidinyl (e.g., 1-pyrrolidinyl), piperidyl (e.g., -piperidyl), piperazinyl (e.g., 1-piperazinyl), morpholinyl (e.g., 4-morpholinyl), pyridyl (e.g., 2-pyridyl), pyrazinyl (e.g., 2-pyrazinyl), pyrimidinyl (e.g., 4-pyrimidinyl), thienyl, furyl, pyranyl, pyrazolyl, isothiazolyl, isoxazolyl, pyridazinyl, furazanyl, pyrrolinyl, imidazolidinyl, imidazolinyl, pyrazolidinyl, or pyrazolinyl may be optionally substituted with one or more (e.g., 0, 1, 2, 3, 4, 5, 6, or 7) of halogen (e.g., F, Cl, Br, or I), hydroxy (—OH), $C_1$-$C_4$ alkyl (e.g., $C_1$, $C_2$, $C_3$, or $C_4$ alkyl), $C_2$-$C_4$ alkenyl (e.g., $C_2$, $C_3$, or $C_4$ alkenyl), $C_2$-$C_4$ alkynyl (e.g., $C_2$, $C_3$, or $C_4$ alkynyl), $C_1$-$C_4$ alkoxy ($C_1$, $C_2$, $C_3$, or $C_4$ alkoxy), aryl, cycloalkyl, heterocyclyl, heteroaryl, methanoly (—COH), carboxy (—$CO_2H$), nitro (—$NO_2$), cyano (—CN), amino (—$NH_2$), carbamoyl (—$CONH_2$), ethynyl (—CCH), —$CF_3$, —$CF_2CF_3$, —$OCF_3$, —$OCF_2CF_3$, or sulfo (—$SO_3H$).

$R_f$ may be the same or different for each choice and may be H or $C_1$-$C_4$ alkyl (e.g., $C_1$, $C_2$, $C_3$, or $C_4$ alkyl). $R_g$ may be the same or different for each choice and may be H or $C_1$-$C_4$ alkyl (e.g., $C_1$, $C_2$, $C_3$, or $C_4$ alkyl).

In one aspect, the compound of Formula (I) may exclude F3:

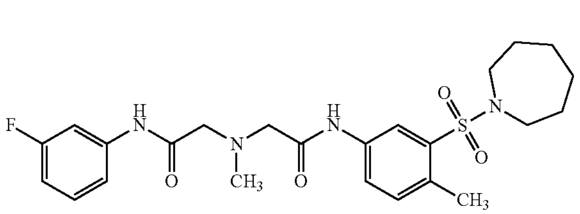 [SMILES: Cc1ccc(NC(=O)CN(C)CC(=O)Nc2cccc(F)c2)cc1S(=O)(=O)N1CCCCCC1]

Preferably $X^1$ is —NH— substituted with $R_X$ or —($CH_2$)—. Preferably $R^1$ is aryl meta substituted with one halogen, aryl, aryl meta substituted with $C_1$ alkyl, aryl ortho substituted with one halogen, aryl meta substituted with —$CF_3$, aryl para substituted with $C_1$ alkyl, aryl meta substituted with $C_1$ alkoxy, aryl para substituted with $C_1$ alkoxy, aryl ortho substituted with $C_1$ alkyl, alkyl-aryl meta substituted with one halogen, $C_3$ alkyl or $C_4$ alkyl, where the preferred halogen is F. Preferably $R^2$ is aryl meta substituted with $SO_2$—$R^3$ and para substituted with $C_1$ alkyl, aryl meta substituted with $SO_2$—$R^3$, aryl meta substituted with —(C═O)—$R^3$ and para substituted with $C_1$ alkyl, aryl, alkyl-heterocyclyl (such as methyl-benzodioxolyl), heterocyclyl (such as benzodioxolyl), aryl meta substituted with $SO_2$—$R^3$ and ortho substituted with $C_1$ alkyl, aryl meta substituted with $SO_2$—$R^3$ and para substituted with $C_3$ alkyl, aryl meta substituted with $SO_2$—$R^3$ and para substituted with $C_2$ alkoxy, aryl meta substituted with $SO_2$—$R^3$ and para substituted —O(($CH_2$)$_2$)—$N(CH_3)_2$, aryl meta substituted with $SO_2$—$R^3$ and para substituted with $C_5$ alkyl, aryl meta substituted with $SO_2$—$R^3$ and para substituted —O(($CH_2$)$_3$)—$N(CH)_2$, aryl meta substituted with $SO_2$—$R^3$ and para substituted —O(($CH_2$)$_6$)—$N(CH_3)_2$, aryl meta substituted with $SO_2$—$R^3$ and para substituted —O(($CH_2$)$_8$)—$N(CH_3)_2$, aryl meta substituted with $SO_2$—$R^3$ and para substituted —O(($CH_2$)$_4$)—$N(CH_3)_2$, or aryl meta substituted with $SO_2$—$R^3$ and para substituted $C_2$ alkoxy. Preferably $R_x$ is methyl. Preferably $R^3$ is $C_{4-7}$ heterocyclyl, —$NR_aR_b$ with $R_a$ $C_2$ alkyl and $R_b$ $C_2$ alkyl, —$NR_aR_b$ with $R_a$ $C_3$ alkyl and $R_b$ H, —$NR_aR_b$ with $R_a$ cycloalkyl and $R_b$ H, or —$NR_aR_b$ with $R_a$ cycloaryl and $R_b$ H. Also included are all the permutations and combinations of these preferred selections of $R^1$, $R^2$, $X^1$, $R_x$ and $R^3$.

Preferably, the compound is capable of interacting with the RAS sequences, or one or more amino acids of the RAS sequence, in particular the compound is suitable for or capable of interacting (e.g., via covalent bond, ionic bond, van der waals force, hydrophobic interaction, steric interaction, hydrophylic interaction, hydrogen bond, or a combination thereof) with one or more of the following amino acids in the RAS reference sequence: ILE 21, ILE 24, GLN 25, HIS 27, VAL 29, LYS 31, ASP 33, PRO 34, THR 35, ILE 36, GLU 37, ASP 38, SER 39, TYR 40, ARG 41, LYS 42, LEU 56, TYR 64, MET 67, GLY 13, GLY 15, LYS 16, SER 17, ALA 18, LEU 19, ILE 21, GLN 22, HIS 27, PHE 28, VAL 29, ASP 30, LYS 31, TYR 32, ASP 33, PRO 34, THR 35, ASP 38, TYR 40, ASP 57, or ALA 146.

A disease associated with activating mutations in RAS, or treatable by a reduction in RAS activity, include cancers and tumors, especially those which have been identified as having an activating RAS mutation. It may be desirable to test a biopsy sample from a patient before treatment with a RAS inhibitor, such as by detecting a mutated RAS gene or genes within the sample. FIG. 1 lists a variety of cancers and tumors which have be found to have a mutant KRAS gene. Other disease which may be treated with a RAS inhibitor include capillary malformation-AV malformation syndrome, autoimmune lymphoproliferative syndrome, cardiofaciocutaneous syndrome, hereditary gingival fibromatosis type 1, neurofibromatosis type 1, noonan syndrome, costello syndrome, legius syndrome, and noonan syndrome with multiple lentigines.

The RAS inhibitor may be administered as a pharmaceutical composition. A pharmaceutical composition is formulated to be compatible with its intended route of administration, including intravenous, intradermal, subcutaneous, oral, inhalation, transdermal, transmucosal, and rectal administration. Administration may be followed by testing for efficacy, followed by one or more administration and testing steps.

A "pharmaceutically acceptable carrier" includes any and all solvents, dispersion media, coatings, antibacterial and antifungal agents, isotonic and absorption delaying agents, solid excipients and the like, compatible with pharmaceutical administration. Preferred examples of such carriers or diluents include water, saline, Ringers solutions and dextrose solution. Supplementary active compounds can also be incorporated into the compositions. Solutions and suspensions used for parenteral administration can include a sterile diluent, such as water for injection, saline solution, polyethylene glycols, glycerin, propylene glycol or other synthetic solvents; antibacterial agents such as benzyl alcohol or methyl parabens; antioxidants such as ascorbic acid or sodium bisulfite; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A pharmaceutical composition is formulated to be compatible with its intended route of administration, including intravenous, intradermal, subcutaneous, oral, inhalation, transdermal, transmucosal, and rectal administration. Solutions and suspensions used for parenteral, intradermal or subcutaneous application can include a sterile diluent, such as water for injection, saline solution, polyethylene glycols, glycerin, propylene glycol or other synthetic solvents; antibacterial agents such as benzyl alcohol or methyl parabens; antioxidants such as ascorbic acid or sodium bisulfite; buffers such as acetates, citrates or phosphates, and agents for the adjustment of tonicity such as sodium chloride or dextrose. The pH can be adjusted with acids or bases, such as hydrochloric acid or sodium hydroxide.

Preferred administration is oral administration, including as a powder, table or capsule, an oral solution or suspension, or sublingual or buccal tablets. Alternative forms of administration include rectal suppositories, inhaled, epidural, subcutaneous, nasal spray, transmucosal, and intradermal formulations. Preferably administration is by unit dosage form. Examples of unit dosage forms include oral compositions, such as tablets (for example, sublingual or buccal tablets), capsules (for example, hard gelatin and soft gelatin capsules), transmucosal and sublingual patches and films, pre-measured powder packets and sachets, flavored and/or sweetened aqueous solutions or suspensions. Preferably, the oral unit dosage form is present as a once-per-day dosage. Excipients and adjuvants may be also be included in any of the unit dosage forms, both oral and non-oral.

Multi-dosage forms, such as kits, containing 2 to 30, 3 to 25, or 5 to 14 unit dosage forms, for example 6, 7, 8, 9, 10, 11, 12, 13, 15, 20, 40, 50 or 60 unit dosage forms, may be provided. Preferably, the multi-dosage forms contain sufficient unit dosage forms for administration over a period of 2 to 30, 3 to 25, or 7 to 14 days, for example 4, 5, 6, 7, 8, 9, 10, 11, 12, 13, 20 or 30 day.

Pharmaceutical compositions suitable for injection include sterile aqueous solutions or dispersions for the extemporaneous preparation of sterile injectable solutions or dispersion. Various excipients may be included in pharmaceutical compositions suitable for injection. For intravenous administration, suitable carriers include physiological saline, bacteriostatic water, CREMOPHOR EL® (BASF; Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. Various antibacterial and antifungal agents, for example, parabens, chlorobutanol, phenol, ascorbic acid, and thimerosal, can contain microorganism contamination. Isotonic agents such as sugars, polyalcohols, such as manitol, sorbitol, and sodium chloride can be included in the composition. Compositions that can delay absorption include agents such as aluminum monostearate and gelatin. Sterile injectable solutions can be prepared by incorporating the compound, and optionally other therapeutic components, in the required amount in an appropriate solvent with one or a combination of ingredients as required, followed by sterilization. Methods of preparation of sterile solids for the preparation of sterile injectable solutions include vacuum drying and freeze-drying to yield a solid.

Topical application may be effective for cancers and potentially-malignant neoplasms present in the skin, for example melanomas, seborrheic keratosis and actinic keratosis. Compositions for topical administration may be in the form of creams or lotions.

An appropriate dosage level of each type RAS inhibitor compound will generally be about 0.01 to 500 mg per kg patient body weight. Preferably, the dosage level will be about 0.1 to about 250 mg/kg; more preferably about 0.5 to about 100 mg/kg. A suitable dosage level may be about 0.01 to 250 mg/kg, about 0.05 to 100 mg/kg, or about 0.1 to 50 mg/kg. Within this range the dosage may be 0.05 to 0.5, 0.5 to 5 or 5 to 50 mg/kg. Although each type of pharmaceutical composition may be administered on a regimen of 1 to 4 times per day, such as once or twice per day, the specific frequency of dosing will depend on the half-life in vivo of the RAS inhibitor. Accordingly, each RAS inhibitor may be administered once a day, once a week, once every two or three weeks, once a month, or once every 60 to 90 days.

However, the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the patient undergoing therapy.

Data in the application showing effective dosages in an animal model may also be used to determine an effective dosage in humans. Guidance is available from the U.S. Department of Health and Human Services [14].

A subject that receives administration of a RAS inhibitor may be tested to determine if it has been effective to treat the cancer, by examining the patient for the spread of the cancer to different parts of the body, particularly in lymph nodes. Any suitable diagnostic test may be used, such as a biopsy, endoscopy, blood test or diagnostic imaging test such as an X-ray or CT scan. Administration of the RAS inhibitor and subsequent testing may be repeated until the desired therapeutic result is achieved. Similarly, a subject may be tested to determine if a potentially-malignant tumor, cancer or neoplasm has been effectively treated by a reduction in size, or disappearance, of the tumor, cancer or neoplasm.

The pharmaceutical composition described herein may further comprise other therapeutically active compounds, and/or may be used in conjunction with physical techniques as noted herein which are suitable for the treatment of cancers and tumors. Examples of commonly used therapeutically active compounds include vinorelbine (Navelbine®), mytomycin, camptothecin, cyclyphosphamide (Cytoxin®), methotrexate, tamoxifen citrate, 5-fluorouracil, irinotecan, doxorubicin, flutamide, paclitaxel (Taxol®), docetaxel, vinblastine, imatinib mesylate (Cleevec®), anthracycline, letrozole, arsenic trioxide (Trisenox®), anastrozole, triptorelin pamoate, ozogamicin, irinotecan hydrochloride (Camptosar®), BCG, live (Pacis®), leuprolide acetate implant (Viadur), bexarotene (Targretin®), exemestane (Aromasin®), topotecan hydrochloride (Hycamtin®), gemcitabine HCL (Cemzar®), daunorubicin hydrochloride (Daunorubicin HCL®), gemcitabine HCL (Gemzar®), toremifene citrate (Fareston), carboplatin (Paraplatin®), cisplatin (Platinol® and Platinol-AQ®) oxaliplatin and any other platinum-containing oncology drug, trastuzumab (Herceptin®), lapatinib (Tykerb®), gefitinb (Iressa), cetuximab (Erbitux®), panitumumab (Vectibix®), temsirolimus (Torisel®), everolimus (Afinitor®), vandetanib (Zactima™), vemurafenib (Zelboraft), crizotinib (Xalkori®), vorinostat (Zolinza®), bevacizumab (Avastin®), immunotherapy, anti-cancer antibodies, anti-nucleolin agents, radiation therapy, hyperthermia, gene therapy and photodynamic therapy. Such agents or treatments may be administered before, after, or simultaneously, with one or more RAS inhibitor described herein. Particularly preferred are administration with an immunotherapy (such as pembrolizumab or nivolumab, which are immune checkpoint inhibitors that block PD-1) or an anti-nucleolin agent (such as AS1411 or AS1411 conjugated to gold nanoparticles).

Any mammal that could develop tumors, cancer or metastatic cancer may be treated by the methods herein described. Humans are a preferred mammal for treatment. Other mammals that may be treated include mice, rats, goats, sheep, camels, cows, horses and companion animals, such as dogs or cats. A subject in need of treatment may be identified by the diagnosis of a tumor or cancer. Any form of tumor or cancer may be treated, including breast cancer, ovary cancer, cervix cancer, skin cancer, lung cancer, colon cancer, pancreatic cancer, colorectal cancer, thyroid cancer, seminoma, melanoma, sarcoma, bladder cancer, liver cancer, kidney cancer, glioma, myeloid cancers (e.g., MDS, IMF, AML, or CML) or lymphoid disorders (e.g., ALL, NHL, Hodgkin's, or hairy cell). Metastatic cancers may also be treated; cancers which are particularly subject to metastasis include lung cancer, melanoma, colon cancer, renal cell carcinoma, prostate cancer, cancer of the cervix, bladder cancer, rectal cancer, esophageal cancer, liver cancer, mouth and throat cancer, multiple myeloma, ovarian cancer, and stomach cancer. Treatment may be of patients experiencing metastatic cancer. Treatment may also be administered to patients who have cancer, but prior to any identified metastasis, in order to prevent metastasis. Similarly, any mammal that could develop potentially-malignant neoplasms may be treated by the methods herein described.

EXAMPLES

Example 1: Synthesis of Compounds

The compounds of Formula I may be prepared by first preparing the corresponding amines $R^1$—$NH_2$ and $R^2$—$NH_2$, followed by sequential reaction with the diacid $X^1$ $(CH_2COOH)_2$, which may optionally be in the form of a cyclic anhydride. In the examples which follow, where $R^1$ and $R^2$ comprise substituted phenyl groups. In the first example the substituted phenyl groups have been labelled "A" and "B", respectively.

Synthesis of Compound F3:

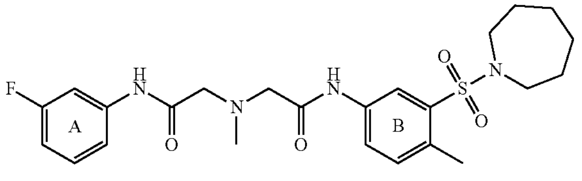

Synthesis of Sulfonamide Fragment:

Scheme 1. Synthesis F3 sulfonamide fragment.

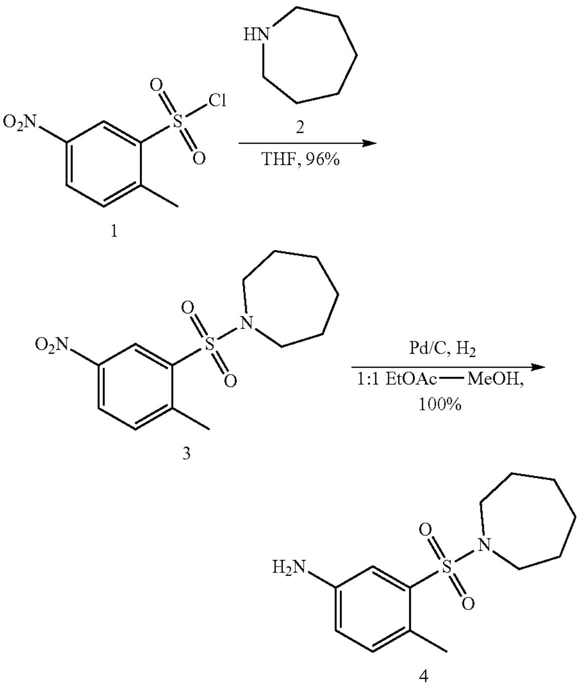

The synthesis of F3 began by constructing sulfonamide 4 (ring B of F3). The sulfonamide was prepared by treating commercially available sulfonyl chloride 1 with two equivalents of amine 2. The synthesis was completed in excellent overall yield by reduction of nitro 3 under catalytic hydrogenation conditions. A variety of sulfonamide derivatives were prepared by replacing 2 with a suitable secondary or tertiary amine.

For some analogs, sulfonyl chlorides were not commercially available and were prepared in one step. Please see the experimental for compound 9 below as an example. Compound 4 is known and prepared from a modified literature preparation [6], Experimental:

1-((2-Methyl-5-nitrophenyl)sulfonyl)azepane 3. To a solution of 2.50 g (10.6 mmol) of sulfonyl chloride 1 in 75 mL of THF at 0° C. was added dropwise 24 mL (2.1 g, 21.2 mmol) of hexamethyleneimine 2. The resulting solution was stirred for 1.5 hrs at 0° C. and 2 hrs at room temperature at which point the reaction was completed as indicated by TLC. The reaction was quenched by slowly adding 90 mL of water and stirring for 5 mins. The layers were separated and the aqueous phase was extracted twice with 100 mL-portions of ethyl acetate. The combined organic layers were washed with brine, dried (sodium sulfate) and filtered through a plug of silica gel (rinsed with ethyl acetate). The solvent was removed in vacuo to afford 3.04 g (96%) of 3 as a dark yellow oil.

3-(Azepan-1-ylsulfonyl)-4-methylaniline 4. To a solution of 3.04 g (10.3 mmol) of aryl nitro 3 in 125 mL of a 1:1 solution of ethyl acetate-methanol was carefully added 400 mg of 10% Palladium on carbon. The suspension was stirred under an atmosphere of hydrogen gas (balloon) for 16 hrs. The suspension was then filtered through a plug of Celite (rinsed with ethyl acetate) and concentrated in vacuo to afford 2.89 g (100%) of aniline 4 as a colorless oil.

Other anilines can be prepared from either synthesized or commercially available sulfonyl chlorides by using a suitable secondary or tertiary amine in place of amine 2.

Synthesis of F3 and Related Derivatives:

Scheme 2. Synthesis of F3 and related derivatives

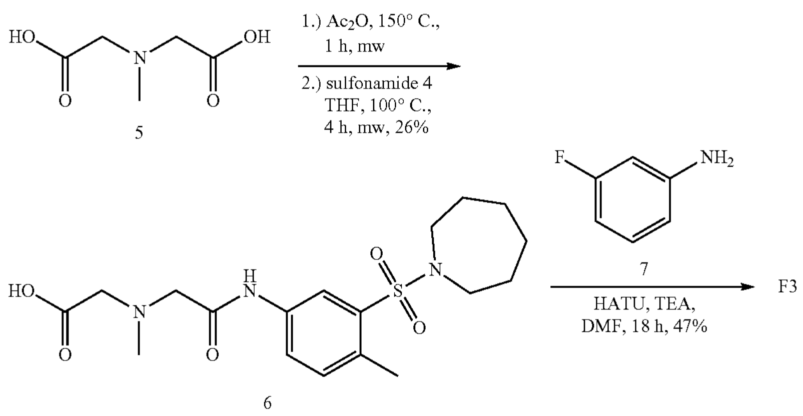

With sulfonamide 4 in hand, the synthesis of F3 began by heating commercially available iminodiacetic acid via microwave irradiation with acetic anhydride to generate a reactive cyclic anhydride [7]. Ring opening with aniline 4 provided the desired acid (6) in good yield [8, 9]. The synthesis of F3 was completed by coupling acid 6 with aniline 7 using HATU/TEA protocol. We found that EDCI gave poor yields. Also, anilines 4 and 7 in the amide forming steps can be swapped (i.e. the aniline 4 or 7 may be used in the first step), Experimental:

2-((2-((3-(Azepan-1-ylsulfonyl)-4-methylphenyl)amino)-2-oxoethyl)(methyl)amino)acetic acid 6. A solution of 500 mg (3.40 mmol) of iminodiacetic acid 5 in 3 mL of acetic anhydride was stirred at 150° C. for 1 h via microwave irradiation. After cooling to room temperature, the solvent was removed in vacuo and the crude intermediate was dried under high vacuum for 5 hrs. The intermediate was dissolved in 20 mL of TH and to the resulting solution was added 913 mg (3.40 mmol) of aniline 4. The reaction was stirred for 4 hrs at 100° C. via microwave irradiation. After cooling to room temperature, the mixture was filtered through a plug of silica gel that was rinsed with ethyl acetate and then with a solution of 1:1 ethyl acetate-methanol. The fraction containing the solution of 1:1 ethyl acetate-methanol was concentrated in vacuo to afford 350 mg of 6 (26%) as a light brown solid.

N-(3-(Azepan-1-ylsulfonyl)-4-methylphenyl)-2-((2-((3-fluorophenyl)amino)-2-oxoethyl)(methyl)amino)-acetamide F3. To a solution of 159 mg (0.400 mmol) of acid 6 and 0.08 mL (89 mg, 0.800 mmol) of aniline 7 in 4 mL of DMF was added 228 mg (0.600 mmol) of HATU and then 0.17 mL (121 mg, 1.20 mmol) of triethylamine. The reaction solution stirred for 18 hrs and then was diluted with 40 mL of water. After stirring for 5 mins, the solution was extracted three times with 30-mL portions of ethyl acetate. The combined organic layers were washed with water and brine. After drying over sodium sulfate, the solvent was removed in vacuo and the crude was chromatographed over silica gel (4 g Combiflash, 0→100% hexanes-ethyl acetate over 11 mins) to afford 93 mg (47%) of F3 as a white foam.

Additional chemistry developed to prepare derivatives:

Synthesis of JAB-7-160

Several compounds were prepared by a different protocol, which includes JAB-7-160, homologs of JAB-7-160, JAB-7-158 and JAB-7-181. These involved preparing densely functionalized anilines.

Scheme 3. Synthesis of JAB-7-160

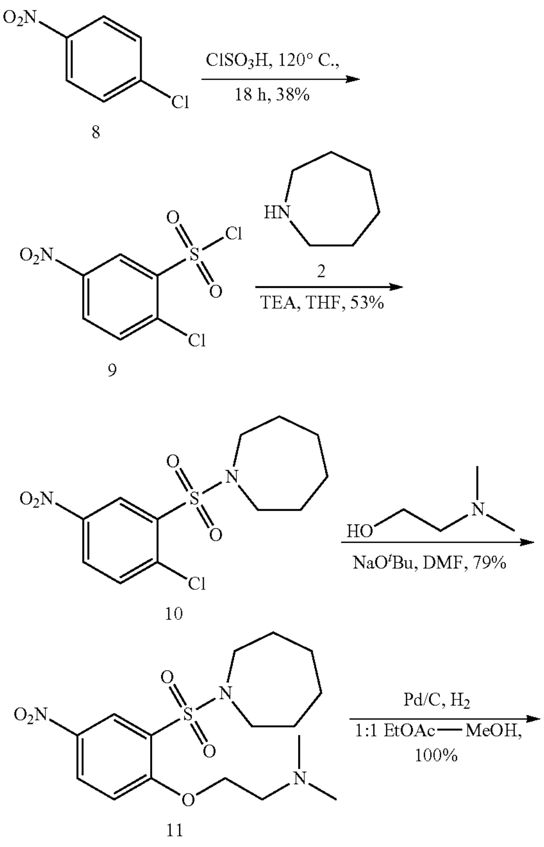

-continued

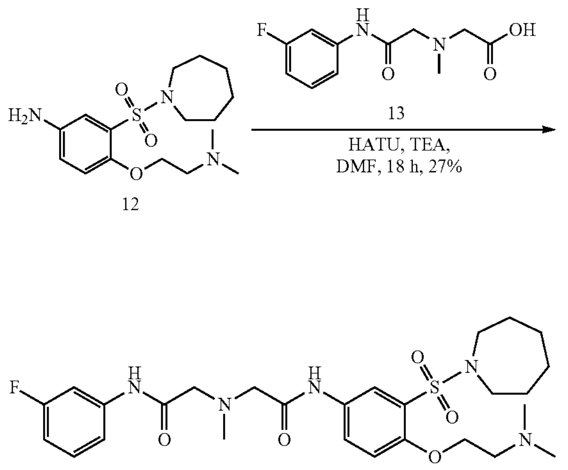

12 13

JAB-7-160

The synthesis began by heating aryl chloride 8 overnight in chlorosulfonic acid to produce sulfonyl chloride 9 [10, 11]. Treatment with hexamethyleneimine 2 afforded sulfonamide 10 in good yield. Careful monitoring of the reaction was required to avoid substitution of the aryl chloride. In the key step, aryl substitution with commercially available 2-(dimethylamino)ethanol in the presence of sodium tert-butoxide produced aryl ether 11 in good yield. The synthesis was complete by hydrogenation of the aryl nitro followed by coupling the resulting aniline (12) with acid 13 utilizing HATU/TEA protocol. Optionally, aryl bromides (but not aryl fluorides) may be used in place of aryl chloride 8.

Derivative JAB-7-158, JAB-8-54, JAB-8-55, JAB-8-60, JAB-8-63, and JAB-8-66 were prepared by a similar method.

Experimental:

2-Chloro-5-nitrobenzene-1-sulfonyl chloride 9. A solution of 1 g (6.35 mmol) of aryl chloride 8 in 3 mL of chlorosulfonic acid (caution!) was stirred at 120° C. for 18 hrs. After cooling to room temperature, the reaction was carefully added dropwise to 150 mL of ice (exothermic!). The aqueous suspension was extracted three times with 75-mL portions of ethyl acetate. The combined organic fractions were washed with brine, dried (sodium sulfate) and concentrated in vacuo. The residue was chromatographed over silica gel (12 g Combiflash, 0→50% hexanes-ethyl acetate, over 11 mins) to afford 620 mg (38%) of 9 as a low-melting, brown solid.

1-((2-Chloro-1-nitrophenyl)sulfonyl)azepane 10. To a solution of 620 mg (2.42 mmol) of sulfonyl chloride 9 in 30 mL of THF at 0° C. was added 0.30 mL (264 mg, 2.66 mmol) of hexamethyleneimine 2 and then 0.33 mL (244 mg, 2.42 mmol) of trimethylamine. The resulting solution stirred for 5 hrs while slowly warming to room temperature. The reaction was complete as indicated by TLC. The reaction was quenched by slowly adding 30 mL of water and stirring for 5 mins. The layers were separated and the aqueous phase was extracted twice with 40-mL portions of ethyl acetate. The combined organic layers were washed with brine, dried (sodium sulfate) and concentrated in vacuo. The residue was chromatographed over silica gel (12 g Combiflash, 0→20% hexanes-ethyl acetate, over 11 mins) to afford 636 mg (53%) of 10 as a yellow solid.

2-(2-(Azepan-1-ylsulfonyl)-4-nitrophenoxy)-N,N-dimethylethanamine 11. To a solution of 90 mg (0.94 mmol) of sodium tert-butoxide in 7 mL of DMF was added dropwise 0.09 mL (76 mg, 0.86 mmol) of 2-(dimethylamino)ethanol. After stirring for 30 mins, a solution of 300 mg (0.94 mmol) of aryl chloride 10 in 4 mL of DMF was added to the reaction mixture. The mixture was stirred at room temperature for 18 hrs and then was quenched by adding 15 mL of water After stirring for 5 mins, the aqueous solution was extracted three times with 10-mL portions of ethyl acetate. The combined organics were dried (sodium sulfate) and concentrated in vacuo. The residue was chromatographed over silica gel (4 g Combiflash, 0→50% ethyl acetate-methanol, over 11 mins) to afford 275 mg (79%) of 11 as a brown oil.

3-(Azepan-1-ylsulfonyl)-4-(2-(dimethylamino)ethoxy)aniline 12. Derivative was prepared as described for the preparation of 4. From 250 mg (0.672 mmol) of aryl nitro 11 was isolated 236 mg (100%) of 12 as a thick syrup.

2-((2-((3-fluorophenyl)amino)-2-oxoethyl)(methyl)amino)acetic acid 13. Derivative was prepared as described for the preparation of 6 except aniline 7 was used instead of the sulfonamide derivative and the crude was purified by chromatography (silica gel, 4 g Combiflash, 0→20% dichloromethane-methanol, over 11 mins). From 566 mg (5.10 mmol) of aniline 7 was isolated 541 mg (44%) of 13 as a brown foam.

N-(3-(azepan-1-ylsulfonyl)-4-(2-(dimethylamino)ethoxy)phenyl)-2-((2-((3-fluorophenyl)amino)-2-oxoethyl)-(methyl)amino)acetamide (JAB-7-160). Derivative was prepared as described for the preparation of F3. Isolated 87 mg (27%) of JAB-7-160 as a brown solid.

Synthesis of JAB-7-181

Scheme 4. Synthesis of JAB-7-181

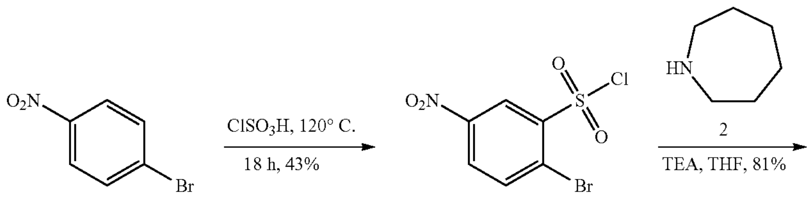

14 15 2

-continued

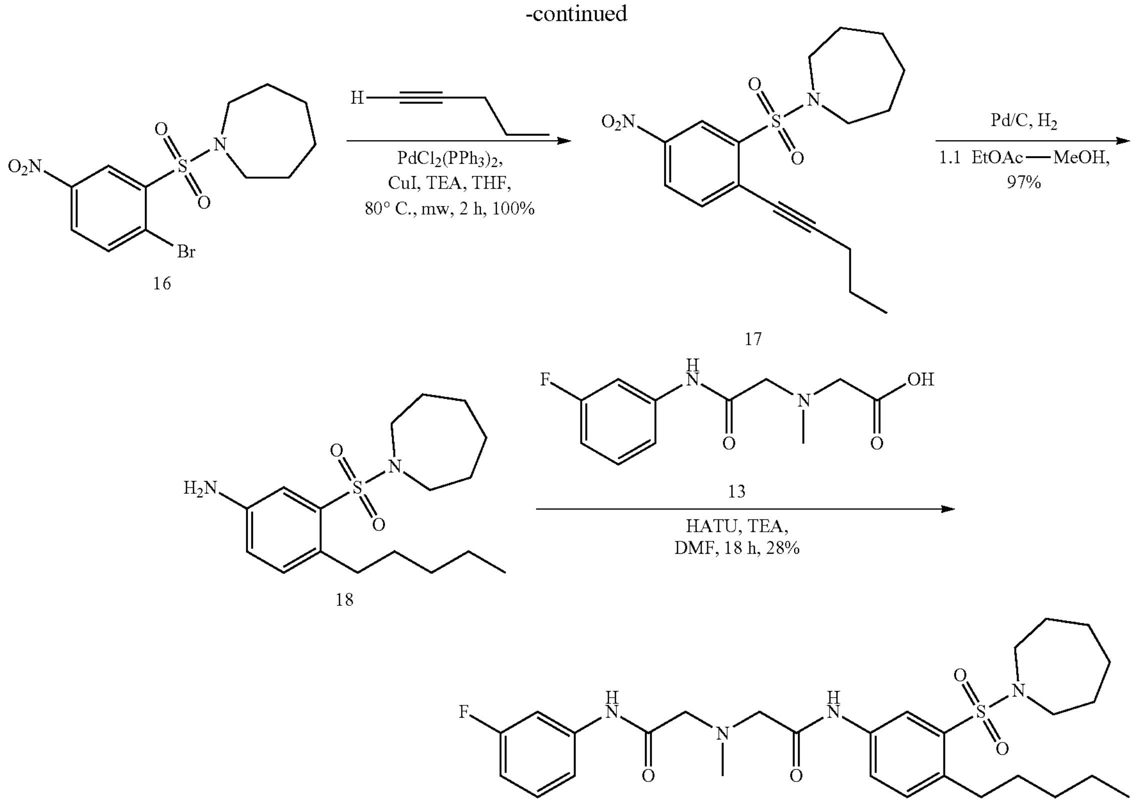

16 17 13 18

JAB-7-181

The synthesis began by heating aryl bromide 14 overnight in chlorosulfonic acid to produce sulfonyl chloride 15 [10, 11]. Treatment with hexamethyleneimine 2 afforded sulfonamide 16 in acceptable yield. Careful monitoring of the reaction was required to avoid substitution of the aryl bromide. In the key step, palladium-catalyzed cross coupling (Sonogashira coupling) between aryl bromide 16 and 1-pentyne proceeded in quantitative yield. After simultaneous hydrogenation of the aryl nitro and alkyne, the synthesis was completed by coupling the resulting aniline (18) with acid 13 utilizing HATU/TEA protocol.

Experimental:

2-Bromo-5-nitrobenzene-1-sulfonyl chloride 15. Derivative was prepared as described for the preparation of 9. From 1.00 g (4.95 mmol) of aryl nitro 14 was isolated 650 mg (43%) of 15 as a low-melting, brown solid.

1-((2-Bromo-5-nitrophenyl)sulfonyl)azepane 16. Derivative was prepared as described for the preparation of 10. From 650 mg (2.16 mmol) of sulfonyl chloride 15 was isolated 640 mg (81%) of 15 as a yellow solid.

1-((5-Nitro-2-(pent-1-yn-1-yl)phenyl)sulfonyl)azepane 17. To a solution of 100 mg (0.302 mmol) of aryl bromide 16 in 3 mL of a 2:1 solution of THF-triethylamine was added 0.04 mL (25 mg, 0.36 mmol) of 1-pentyne, 3.0 mg (0.15 mmol) of copper(I) iodide and 11 mg (0.15 mmol) of bis(triphenylphosphine)palladium(II) dichloride. The solution was degassed and then stirred at 80° C. for 2 h under microwave irradiation. The resulting solution continued to stir at room temperature overnight and then was filtered through a plug of silica gel (rinsed with ethyl acetate). The solvent was removed in vacuo and the residue was chromatographed over silica gel (4 g Combiflash, 0→15% hexanes, ethyl acetate over 11 mins) to afford 111 mg (100%) of 17 as a brownish oil.

3-(Azepan-1-ylsulfonyl)-4-pentylaniline 18. Derivative was prepared as described for the preparation of 4. From 111 mg (0.317 mmol) of aryl nitro 17 was isolated 100 mg (97%) of 18 as a yellow semisolid.

N-(3-(Azepan-1-ylsulfonyl)-4-pentylphenyl)-2-((2-((3-fluorophenyl)amino)-2-oxoethyl)(methyl)amino)acetamide (JAB-7-181). Derivative was prepared as described for the preparation of F3. From 105 mg (0,324 mmol) of aniline 18 was isolated 49 mg (28%) of JAB-7-181 as a white foam.

In addition to F3, the structures of the compounds synthesized are shown below:

JAB-6-1

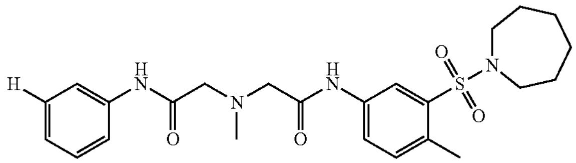

JAB-6-4

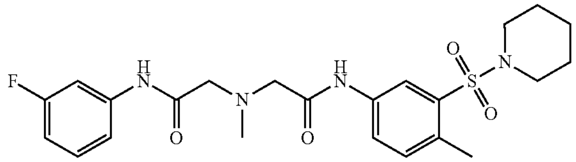

-continued
JAB-6-5
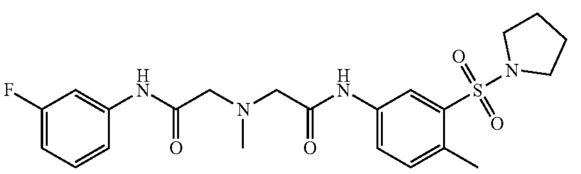
JAB-6-10
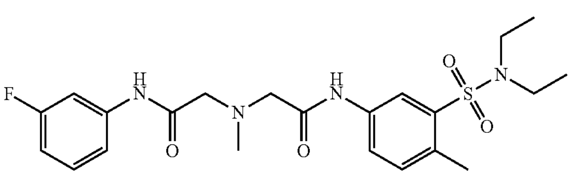
JAB-6-11
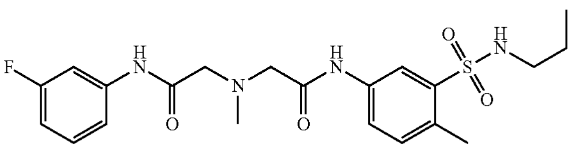
JAB-6-18
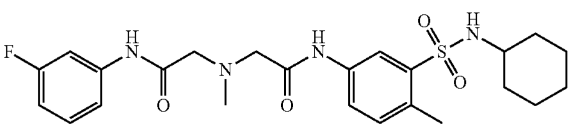
JAB-26
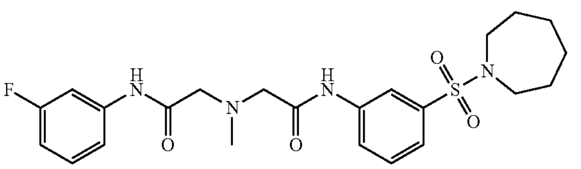
JAB-6-41
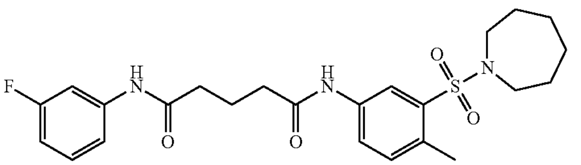
JAB-6-46
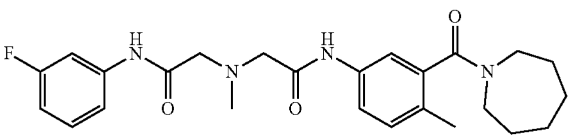
JAB-6-48
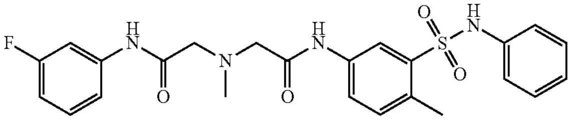
JAB-6-49
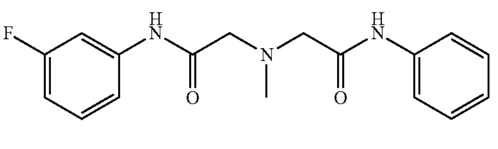
-continued
JAB-6-50
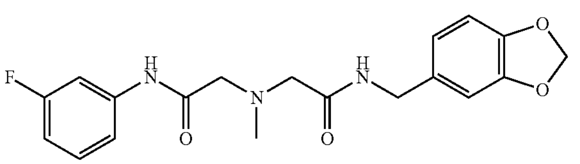
JAB-6-51
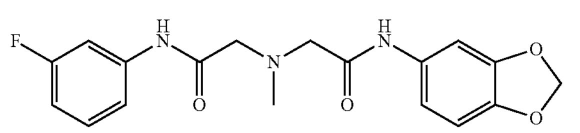
JAB-6-144
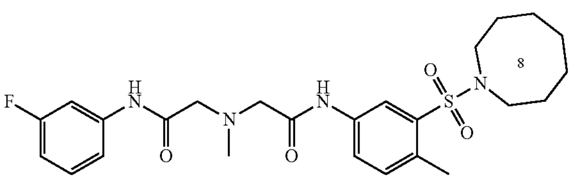
JAB-6-149
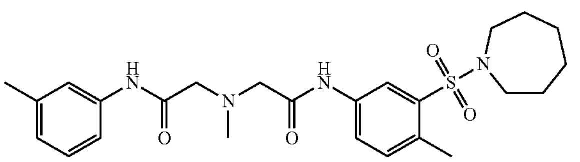
JAB-6-150
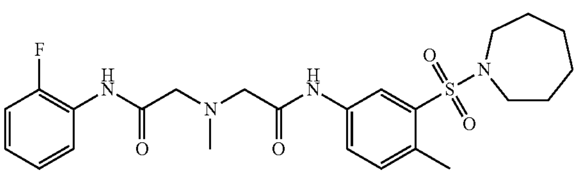
JAB-6-151
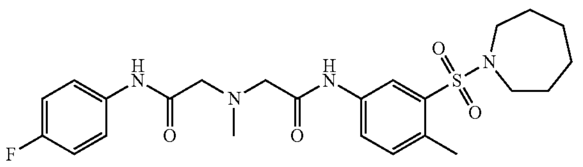
JAB-6-152
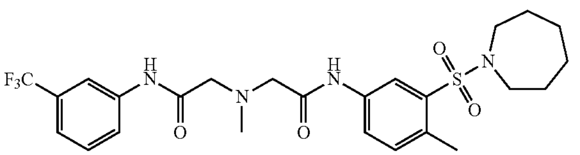
JAB-6-153
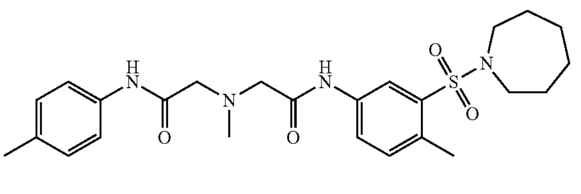

-continued
JAB-6-156
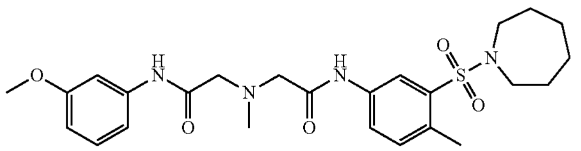
JAB-6-159
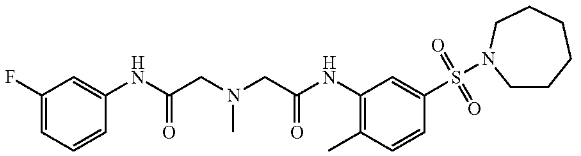
JAB-6-162
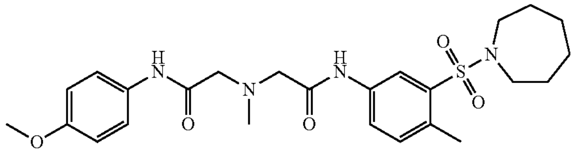
JAB-6-163
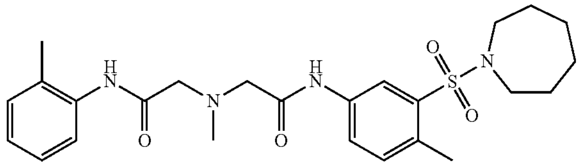
JAB-6-164
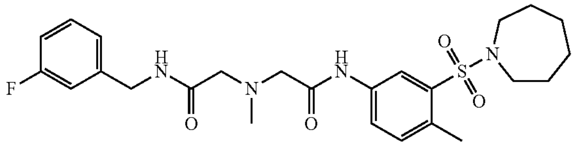
JAB-6-165
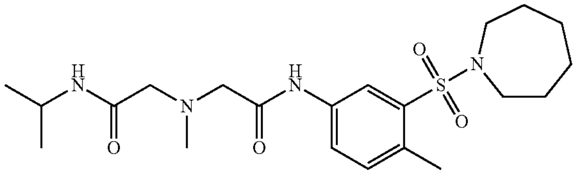
JAB-6-166
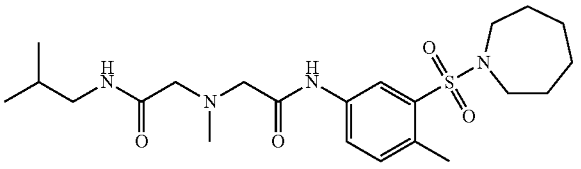
JAB-6-175
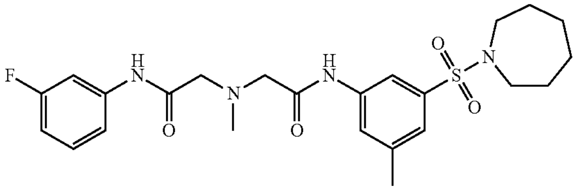
-continued
JAB-6-176
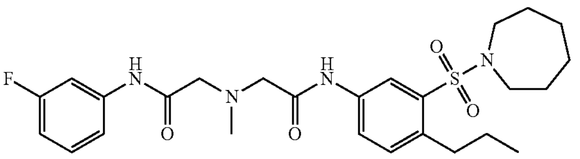
JAB-7-158
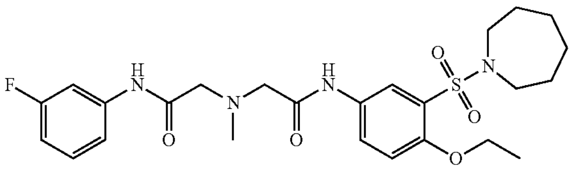
JAB-7-160
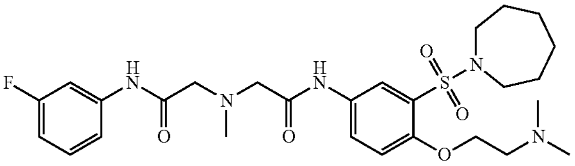
JAB-7-181
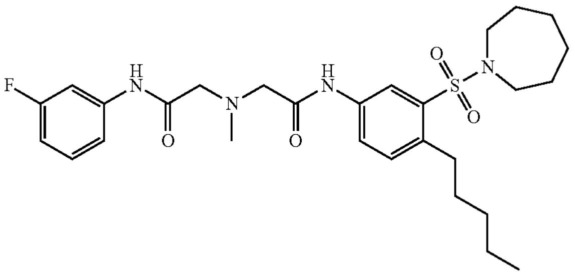
JAB-8-54
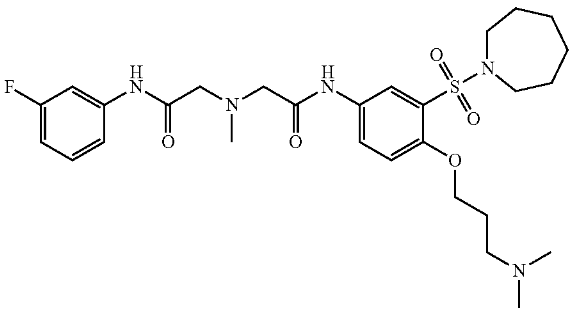
JAB-8-55
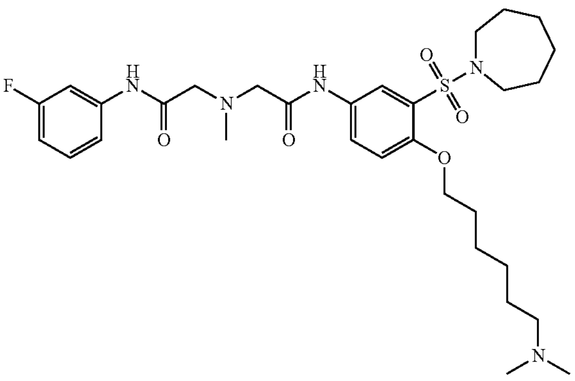

-continued

JAB-8-60

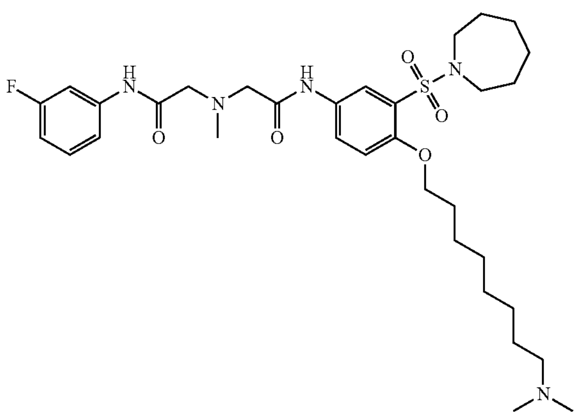

JAB-8-63

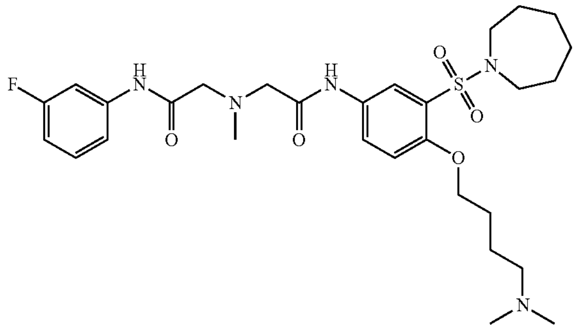

JAB-8-66

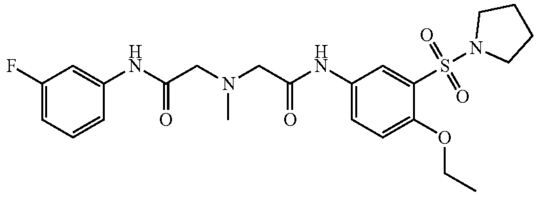

or

JAB-8-68

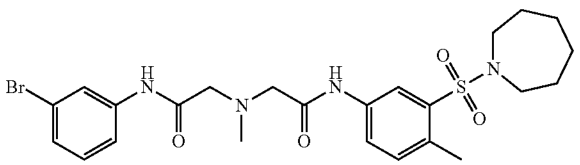

Example 2: Testing of Compounds

Binding Assays

Figure 16:
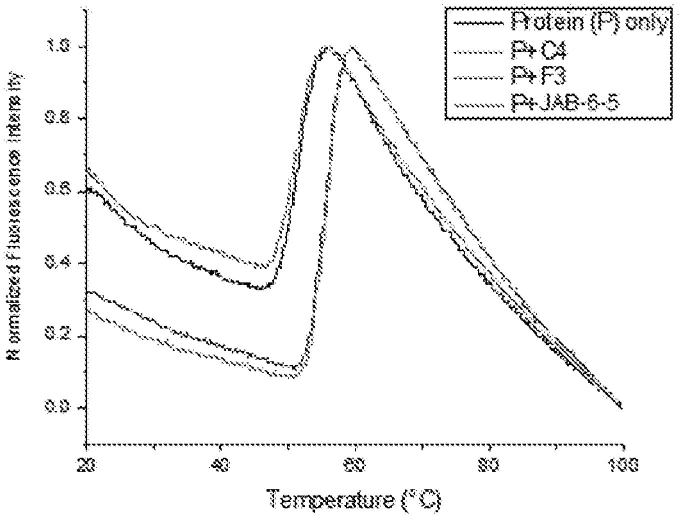
FIG. 16 is a graph showing direct binding of F3/F3a derivative to recombinant K-RAS protein.

Direct binding of F3/F3a derivative to recombinant K-RAS protein. Thermofluor assays were performed to assay whether direct interactions could be detected between recombinant K-RAS protein and compound F3, or recombinant K-RAS protein and compound JAB-6-5. Recombinant K-RAS12v protein was loaded with gamma GTPS and used in binding assays with a ratio of: 200 uM compound/5 uM protein. Control compound C4 is targeted at a different protein and was not expected to bind RAS. The results are the derivative of three assays performed in triplicate. A significant curve shift is observed for both F3 and JAB-6-5 but not C4. A predicted kD can be extrapolated from the curve: ~25 uM at 55.5° C. The results are shown in FIG. 16.

3-D Soft Agar Drug Screening (In Vitro Assay)

The vast majority of solid tumors arise from epithelial cells. Normal epithelial cells in the body live/grow on a basement membrane structure. To grow such cells in vitro, they are cultured in 2-D on coated plastic tissue culture ware. The adherence to the plastic resembles the natural growth on the basement membrane and provides essential survival signals to the cells from integrin interactions with the solid 2-D surface. If these non-cancer cells are suspended in culture medium away from the solid surface, they lose the integrin survival signaling and die by a process called anoikis, which is a type of programmed cell death.

Tumor cells have acquired mutations in oncogenes such as RAS. Mutations in RAS cause constitutive activation of the protein and one of the consequences of this is that some of the tumor cells become independent of integrin survival signals because the RAS signaling compensates for them. Thus, they no longer need to grow on a basement membrane in 2-D. This feature allows them to grow into tumors. It also allows such cells to grow in 3-D culture systems in vitro, which normal cell cannot. Indeed, the ability to grow in 3-D culture closely correlates with the ability to form tumors in animals [12].

Thus, standard growth of tumor cells in 2-0 does not necessarily absolutely require RAS dysfunction but growth in 3-, as in a real tumor, does. This means that assays for RAS inhibitory molecules are most sensitive when performed against cells growing under 3-D (RAS dependent) growth conditions rather than standard 2-D (not completely RAS dependent).

The technical process of 3-D culture involves preparing molten agar at 1.6% in culture medium and adding serum to 10%. 1 ml of this agar medium is plated per well in a 12 well plate and allowed to set. This is the bottom agar and prevents any cells added to the well from touching the plastic bottom of the plate, ensuring everything remains suspended. Meanwhile the remaining stock of agar medium is kept at 42° C. to prevent setting. Target cells are then trypsinized into a single cell suspension and mixed with normal medium/drug combination. ⅔ volume molten agar medium is then added and the mixture plated onto the bottom agar. The agar/medium sets as it cools, suspending the cells in a 3D environment. Typically, within 2 weeks, tumor spheres (colonies) will form suspended in the agar. The number of colonies, or even the size, may be counted under an inverted microscope and quantified to assay tumor sphere inhibition.

The compounds synthesized were tested in the 3-D soft agar drug screening, including F3, JAB-6-176 and JAB-8-60. All the compounds tested suppressed 3-D soft agar growth, but had little effect on normal 2-D growth. This suggests the compounds will have low toxicity to normal, non-tumor cells. In Table 2, below, are listed different cell lines, with the results of testing F3 in the "REMARKS" column. All the cell lines are common and publicly available from the ATCC repository (www.atcc.org/en/Products/Cells_and_Microorganisms/Cell_Lines.aspx). NF1 mute are cells with defects in the NF1 gene (a negative regulator of RAS) causing hyper-activation of the wild type form of RAS. The same is true for DAB2IP deficient cells. EGFR+++ cells overexpress the EGFR receptor, which also results in the hyper-activation of wild type RAS,

TABLE 2

| CELL LINE | GENETICS | TISSUE | REMARKS |
|---|---|---|---|
| Mia-Paca-2 | K12C | Pancreatic | Soft agar growth inhibited |
| A549 | K12S | Lung | Soft agar growth inhibited |
| Panc-1 | K12D | pancreatic | Soft agar growth inhibited |
| H1299 | Hras61 | Lung | Soft agar growth inhibited |
| CaoV3 | NF1mute | ovarian | Soft agar growth inhibited |
| S462.TY | NF1-mute | MPNST | Soft agar growth inhibited |
| A375 | B-RAF mute* | melanoma | Very modest effect at 10 uM, no effect at 2 uM |
| HTB-185 | DAB2IP deficient | Medullo-blastoma | Soft agar growth inhibited |
| MDA-MB-231 | Kras13D and deficient for NF1 | Breast | Don't grow well in soft agar but appear to be inhibited. |
| SK-RC-45 | EGFR++++ | kidney | Soft agar growth inhibited |
| HL-60 | NRASQ61L | AML | Suspension culture, growth in suspension is inhibited |

*Mutant B-RAF should be RAS independent and therefore resistant.

Figure 3:
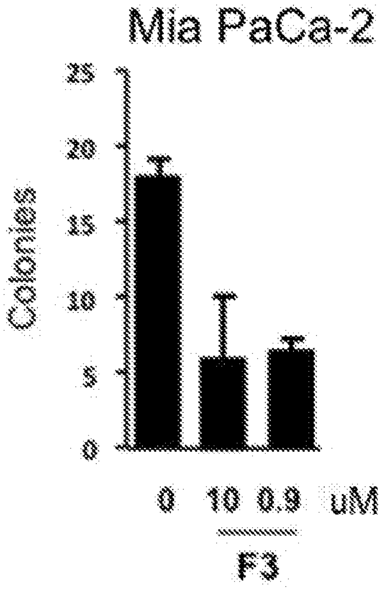
FIG. 3 is a graph showing the specific inhibition of the tumorigenic phenotype Mia PaCa-2 by the small molecule RAS inhibitor F3.
Figure 4:
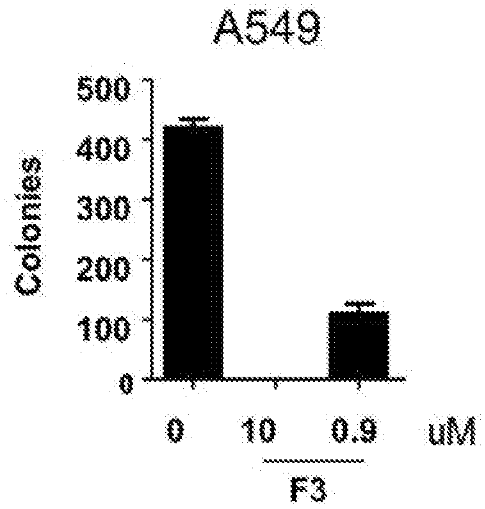
FIG. 4 is a graph showing the specific inhibition of the tumorigenic phenotype A549 by the small molecule RAS inhibitor F3.
Figure 5:
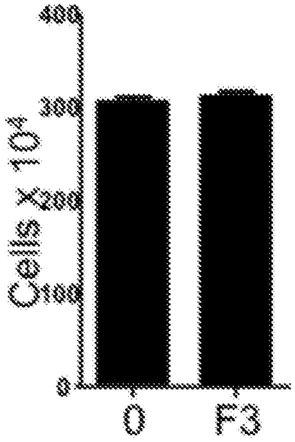
FIG. 5 is a graph showing the effects of 10 uM of F3 on normal growth/survival in 2-D culture on plastic of Mia PaCa-2 cells.
Figure 6:
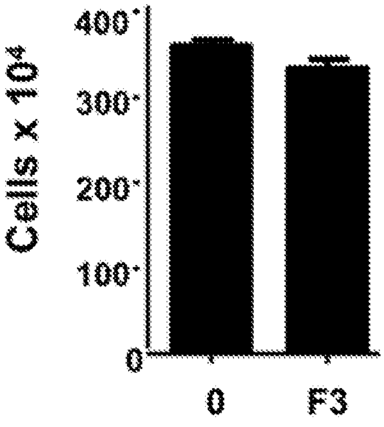
FIG. 6 is a graph showing the effects of 10 uM of F3 on normal growth/survival in 2-D culture on plastic of A549 cells.
Figure 7:
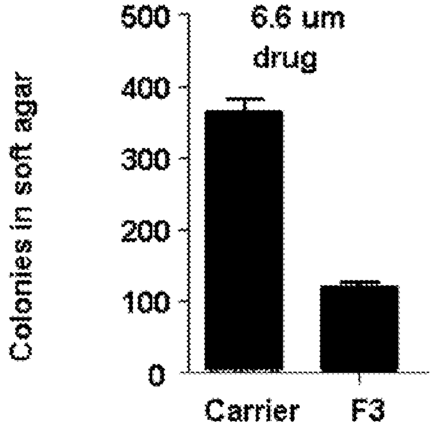
FIG. 7 is a graph showing that F3 is also effective against wild-type RAS driven tumor cells.
Figure 8:
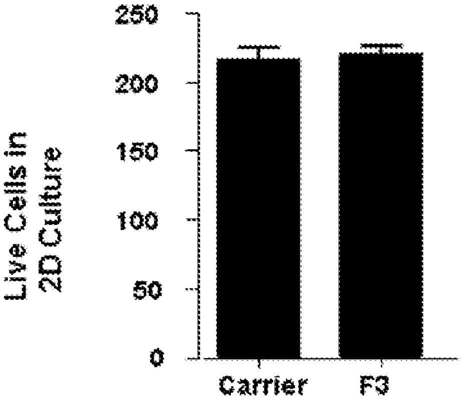
FIG. 8 is a graph showing normal growth/survival in 2-D culture on plastic of wild-type RAS driven tumor cells.

FIG. 3 and FIG. 4 are graphs showing the specific inhibition of the tumorigenic phenotype by the small molecule RAS inhibitor F3. Effects of the small molecule on growth in soft agar of A549 K-RAS driven lung tumor cell line and K-RAS driven pancreatic cancer cell line MiaPaCa-2 is shown. 0=carrier (DMSO). P values are less than 0.05, FIG. 5 and FIG. 6 show the effects of 10 uM of F3 on normal growth/survival in 2-D culture on plastic of the same cells. Analysis of the effects of the drugs on the normal growth on plastic showed that the drug had no effect on cell growth in 2-D, even at 10 uM. FIG. 7 is a graph showing that F3 is also effective against wild-type driven tumor cells, while FIG. 8 is a graph showing normal growth/survival in 2-D culture on plastic of the same cells.

Figure 9:
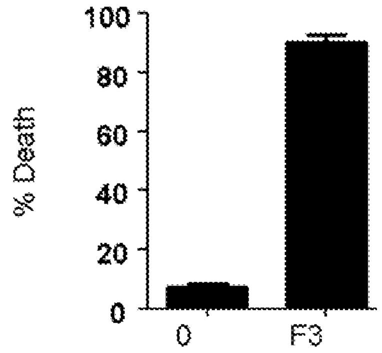
FIG. 9 is a graph illustrating that F3 induced high levels of anoikis

RAS activation leads to resistance to anoikis and inhibiting RAS function re-sensitizes RAG transformed cells to anoikis. The RAS/RalGDS pathway has been implicated as a significant component of RAS mediated anoikis suppression. To demonstrate this effect, Mia-Paca-2 cells were plated in tissue culture wells that had been treated with polyHEMA in order to prevent cell attachment. After 48 hours the cultures were assayed for cell death by trypan blue exclusion. It was found that F3 induced high levels of anoikis. FIG. 9 is a graph illustrating these results.

Figure 10:
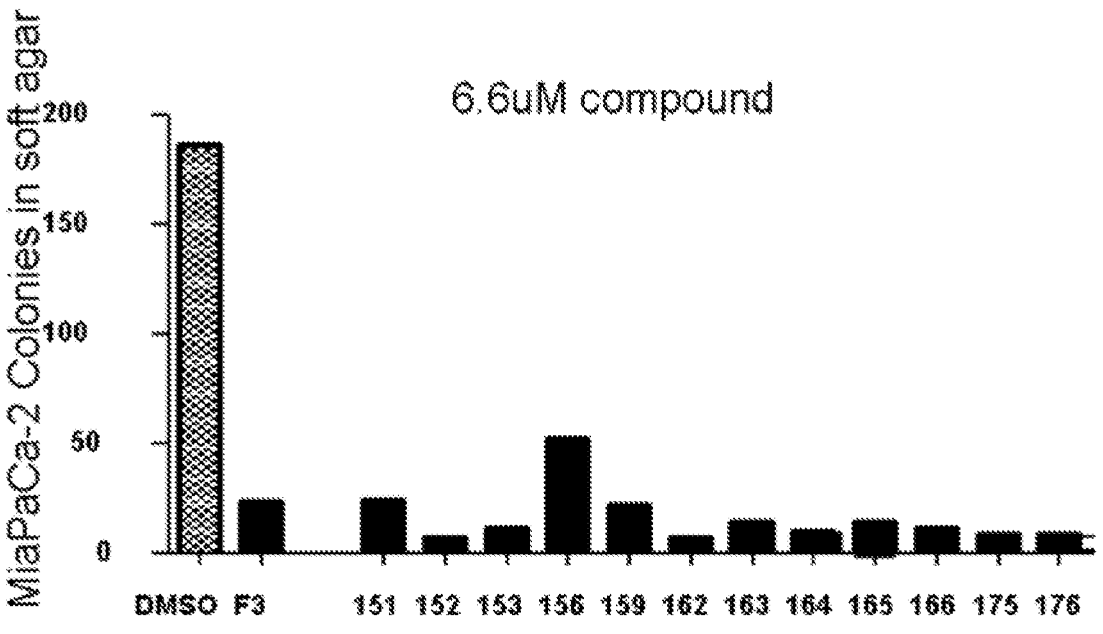
FIG. 10 illustrate the results of testing 12 compounds (JAB-6 compounds) together with F3 in the 3-D soft agar drug screening, at a concentration of 6.6 uM.
Figure 11:
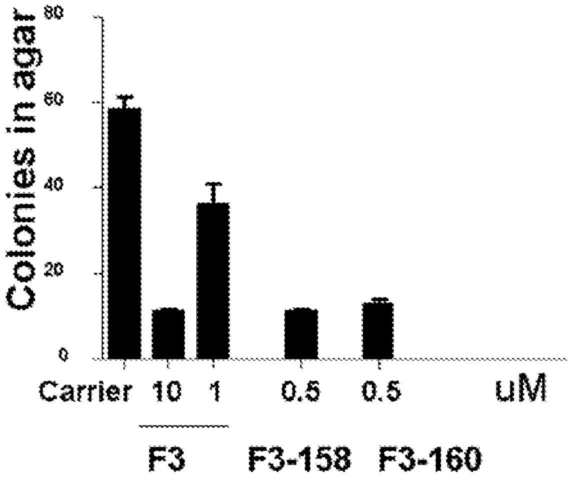
FIG. 11 illustrates the results of testing JAB-6-158 and JAB-6-160 at 0.5 uM in 3-D soft agar drug screening.
Figure 12:
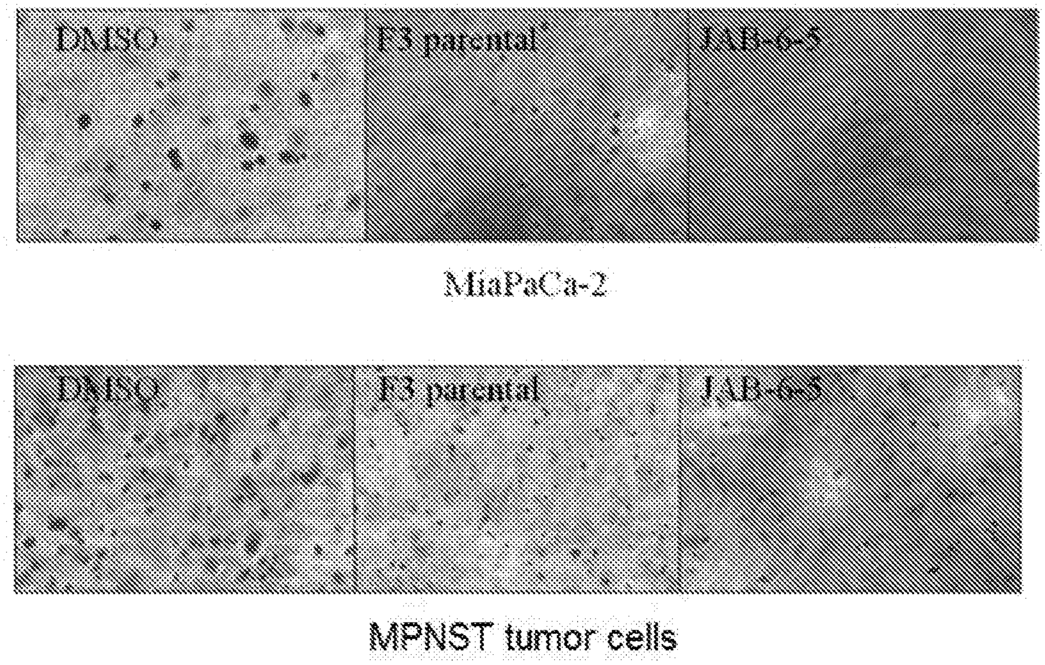
FIG. 12 is photographs showing colonies in soft agar of malignant peripheral nerve sheath tumor cells (MPNST tumor cells) and Mia-Paca-2 cells, treated with DMSO (control), F3 and JAB-6-5.

FIG. 10 illustrate the results of testing 12 additional compounds (JAB-6 compounds) together with F3 in the 3-D soft agar drug screening, at a concentration of 6.6 uM. FIG. 11 illustrates the results of testing JAB-6-158 and JAB-6-160 at 0.5 uM in the same assay. FIG. 12 are photographs showing the colonies in soft agar of malignant peripheral nerve sheath tumor cells (MPNST tumor cells) and Mia-Paca-2 cells, treated with DMSO (control), F3 and JAB-6-5. This data demonstrates that all compounds with Formula I would be expected to inhibit RAS function.

Tumor Inhibition of Xenografts Mice (In Vivo Assay)

Figure 13:
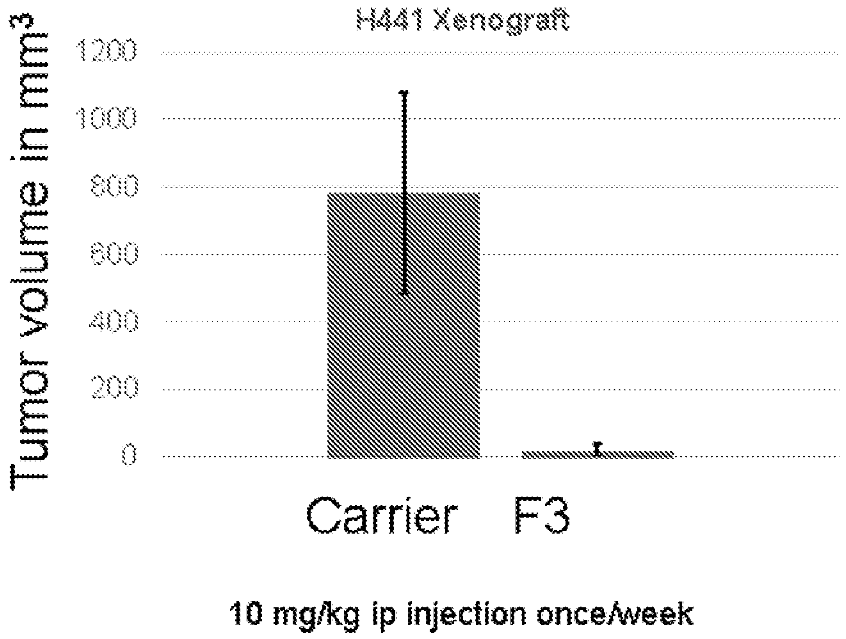
FIG. 13 is a graph showing the results of testing F3 in vivo, using cell line NCI-H441 xenograft tumors in NRG mice.
Figure 14:
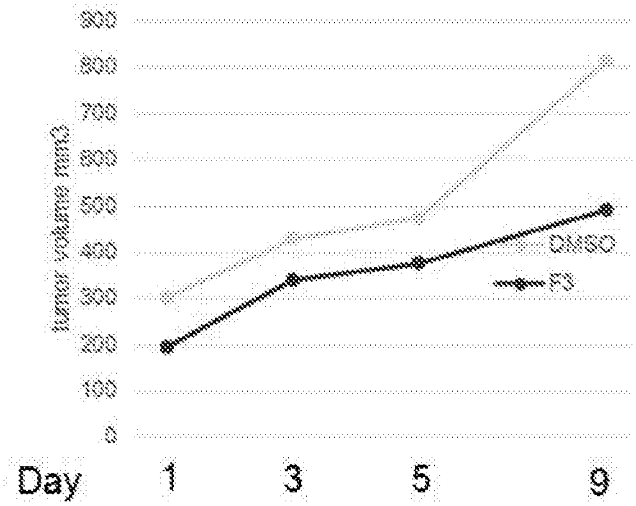
FIG. 14 is a graph showing the results of testing F3 in vivo, using cell line Mia-Paca-2 xenograft tumors in NRG mice.
Figure 15:
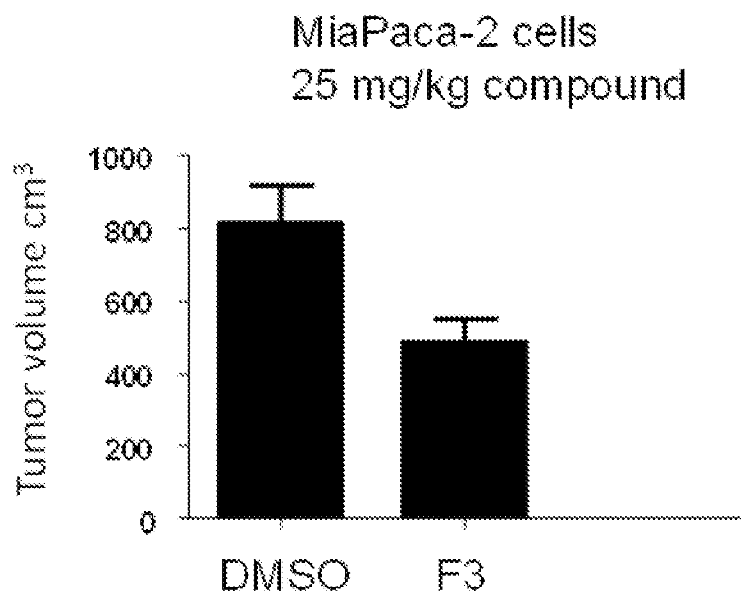
FIG. 15 is a graph showing the results of testing F3 in vivo, using cell line Mia-Paca-2 xenograft tumors in NRG mice.

Compound F3 was tested in vivo, using cell line xenograft tumors in NRG mice. Cell lines used included Mia-Paca-2 (Pancreatic cancer), and NCI-H441 (Lung cancer). The tests showed a reduction in tumor volume as compared to controls. The results for NCI-H441 are shown in FIG. 13. The results for Mia-Paca-2 are shown in FIG. 14 and FIG. 15 (NR mice treated with DMSO/PBS (carrier) or F3 drug at 12 mg/kg every three days). With Mia-Paca-2, tumors that arose in the F3 treated animals were approximately half the volume (P value for the experiment was 0.014).

Pharmacokinetics (In Vivo)

Figure 17:
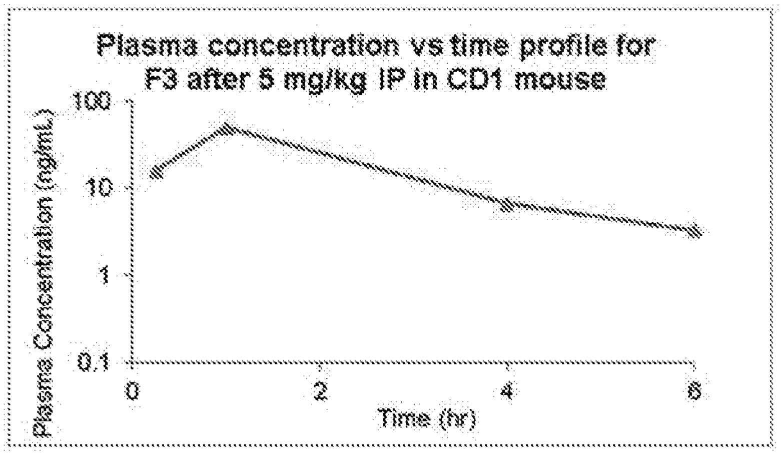
FIG. 17 is a graph showing the plasma concentration of a RAS inhibitor in vivo in CD1 mice.
Figure 18:
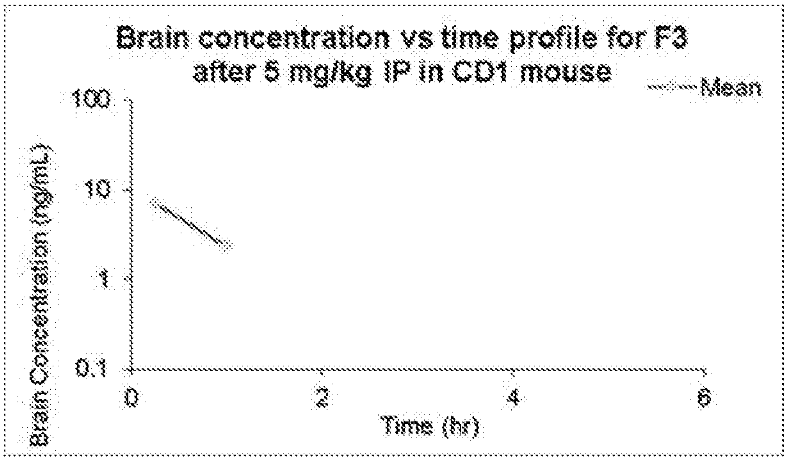
FIG. 18. is a graph showing the concentration in brain of a RAS inhibitor in vivo in CD1 mice.
Figure 19:
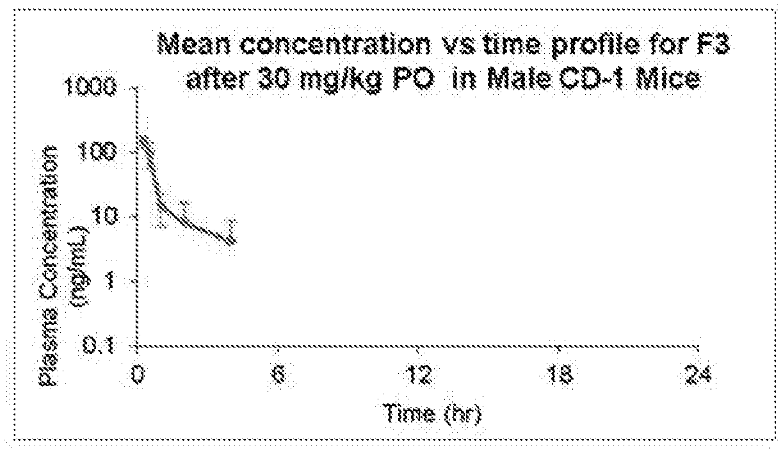
FIG. 19 is a graph showing the plasma concentration of a RAS inhibitor in vivo in CD1 mice, after oral administration.

In order to determine the clearance rate of a RAS inhibitor in vivo, CD1 mice were injected 5 mg/kg IP with F3. The plasma concentration over time was measured. The results are shown in FIG. 17. Similarly, the concentration in brain was also measured, with the results shown in FIG. 18. Plasma concentration after administration orally at 30 mg/kg was measured, with the results shown in FIG. 19.

Toxicity (In Vivo)

A preliminary in vivo toxicity assay was performed on F3. NRG mice were i.p. injected with 10 mg/kg of drug every other day for 2 weeks. No obvious signs of pain or distress were observed, no weight loss was observed. Therefore, the compounds do not appear to be particularly toxic in vivo at this level.

Figure 20:
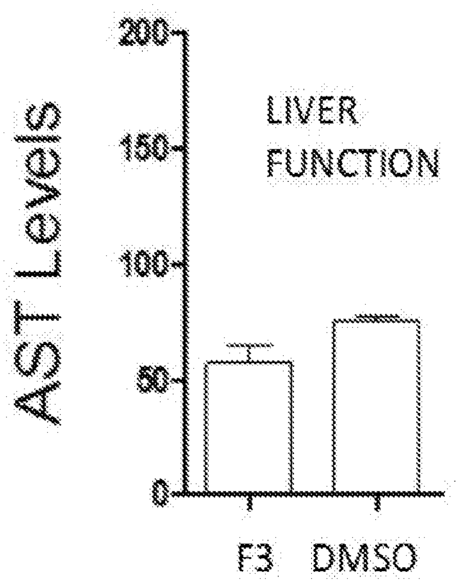
FIG. 20 is a graph showing the effect of F3 on liver function.
Figure 21:
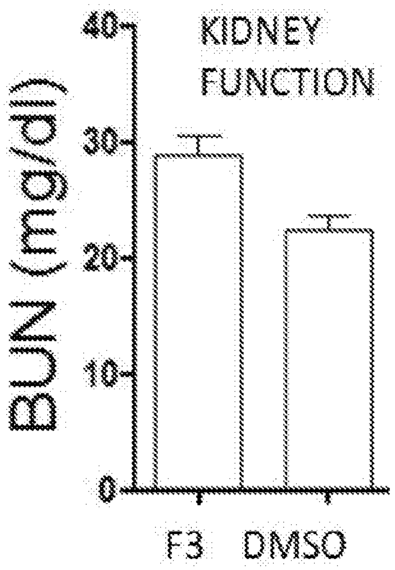
FIG. 21 is a graph showing the effect of F3 on kidney function.

To test for liver toxicity and kidney function, mice were injected with F3 or DMSO as a control, and blood levels of aspartate aminotransferase (AST) and blood urea nitrogen (BUN) were measured. The results are shown in FIG. 20 and FIG. 21.

REFERENCES

1. Hobbs G A, Der C J, Rossman K L. RAS isoforms and mutations in cancer at a glance. *J Cell Sci.* 2016 Apr. 1; 129(7):1287-92.
2. American Cancer Society. Cancer Facts and Figures 2017.
3. Ostrem J M, Peters U, Sos M L, Wells J A, Shokat K M. K-RAS(G12C) inhibitors allosterically control GTP affinity and effector interactions. *Nature.* 2013; 503(7477): 548-551.
4. Shima F, Yoshikawa Y, Ye M, et al. In silico discovery of small-molecule RAS inhibitors that display antitumor activity by blocking the RAS-effector interaction. *Proc Natl Acad Sci USA.* 2013:110(20):8182-8187.
5. Welsch M E, Kaplan A, Chambers J M, et al. Multivalent Small-Molecule Pan-RAS Inhibitors, *Cell,* 2017; 168(5): 878-889.e29.
6. Han, C.; Kim, J. U.; Yoon, J. H.; Lee, S. U.; Kim, N. D.; Jung, Y. S.; Lee, Y. H. Park, S. J.; Shin, J. C.; Yang, J, W. "2-Phenyl-4-[3-(substituted-sulfonyl) anilino]quinazoline derivative for the treatment of hepatitis C and preparative method thereof." KR patent. KR 2012048223, May 15, 2012
7. Burke, M. D.; Dick, G. R.; Knapp, D. M.; Gillis, E. P.; Klubnick, J. A. "Methods for forming protected organoboronic acids," US 20110201806 A1. Aug. 18, 2011.
8. Henry, D. W, "A facile synthesis of piperazines from primary amines," *J. Heterocyclic Chem.* 1966, 3, 503-511,
9. Yamaoka, N.; Kodama, H.; Izuhara, Y.; Miyata, T.; Meguro, K. "Structure-activity relationships of new N-acylanthranilic acid derivatives as plasminogen activator inhibitor-1 inhibitors," *Chem. Pharm. Bull.,* 2011, 59, 215-224.
10. Kil, K.-E.; Poutiainen, P.; Zhang, Z.; Zhu, A.; Kuruppu, D.; Prabhakar, S.; Choi, J.-K.; Tannous, B. A.; Brownell, A.-L. "Synthesis and evaluation of N-(methylthiophenyl) picolinamide derivatives as PET radioligands for metabotropic glutamate receptor subtype 4." *Bioorg. Med. Chem. Let.* 2016, 26, 133-139.

11. Aono, T.; Endo, M. "2-Chloro-5-nitrobenzenesulfonamide," JP patent, JP 60233051, Nov. 19, 1985.

12. Colburn N H, Bruegge W F, Bates J R, Gray R H, Rossen J D, Kelsey W H, et al. Correlation of anchorage-independent growth with tumorigenicity of chemically transformed mouse epidermal cells. *Cancer Res* 1978; 38:624-34.

13. Stedman, T. L. 2000. Stedman's medical dictionary. Lippincott Williams & Wilkins, Philadelphia, xxxvi, [127], 2098.

14. "Guidance for Industry: Estimating the Maximum Safe Starting Dose in Initial Clinical Trials for Therapeutics in Adult Healthy Volunteers" (July 2005) by U.S. Department of Health and Human Services, Food and Drug Administration, Center for Drug Evaluation and Research CDER.

What is claimed is:

1. A compound selected from the group consisting of

JAB-6-1

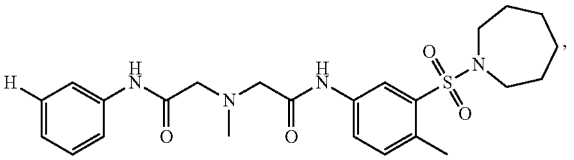

JAB-6-4

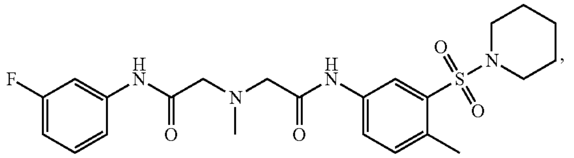

JAB-6-5

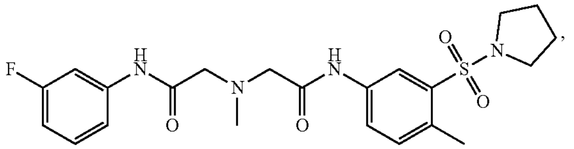

JAB-6-10

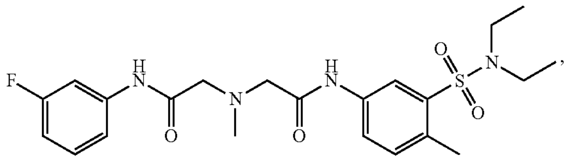

JAB-6-11

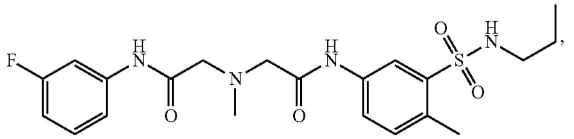

JAB-6-18

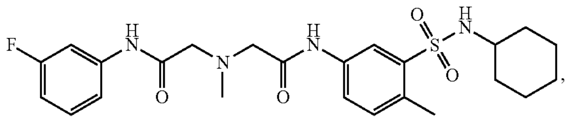

-continued

JAB-6-41

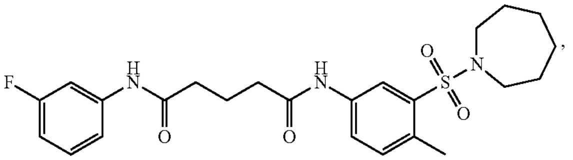

JAB-6-46

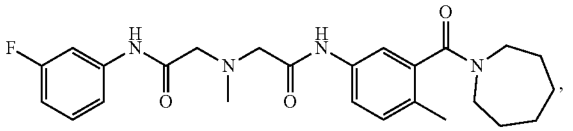

JAB-6-48

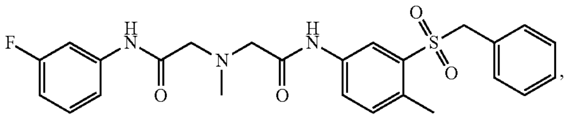

JAB-6-50

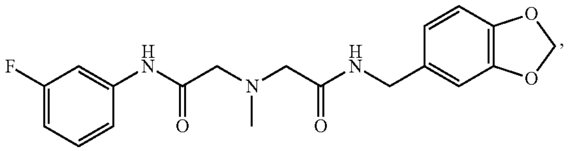

JAB-6-144

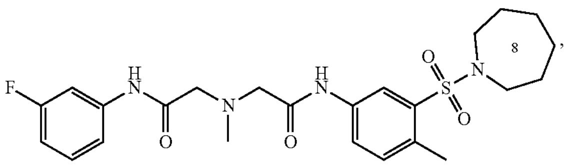

JAB-6-149

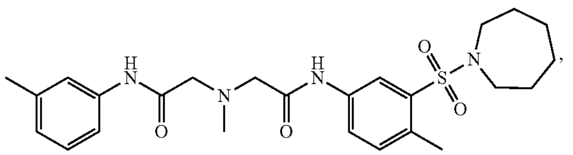

-continued
JAB-6-150
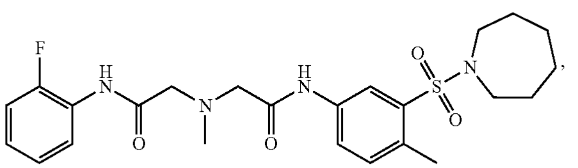
JAB-6-151
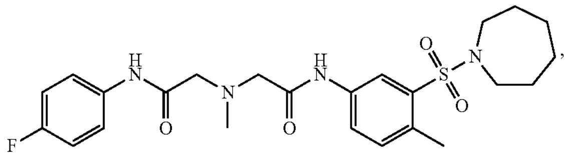
JAB-6-152
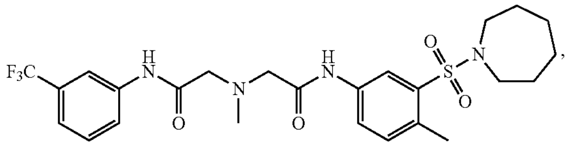
JAB-6-153
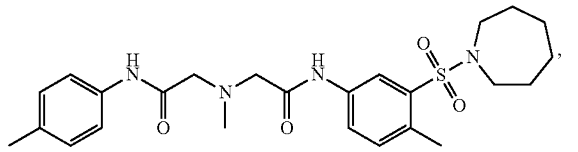
JAB-6-156
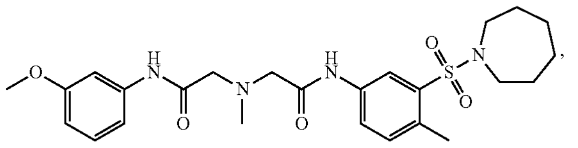
JAB-6-159
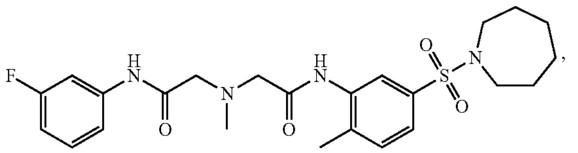
JAB-6-162
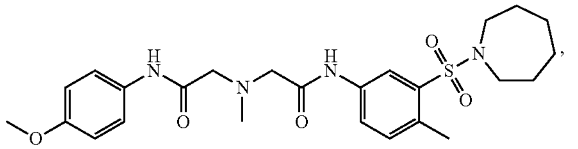
JAB-6-163
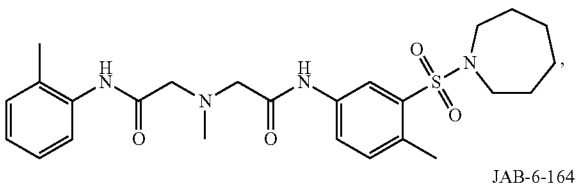
JAB-6-164
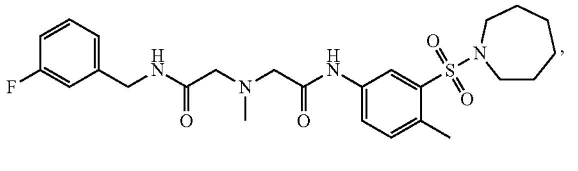
-continued
JAB-6-165
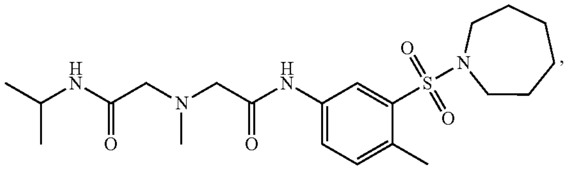
JAB-6-166
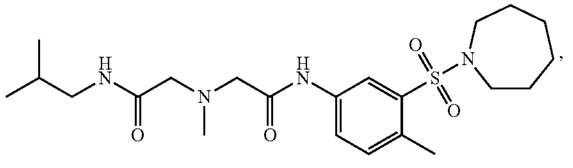
JAB-6-175
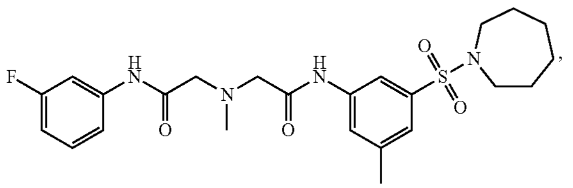
JAB-6-176
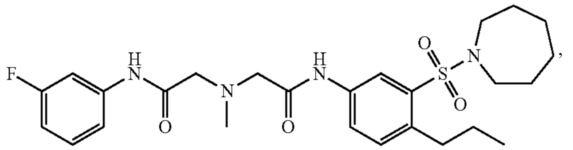
JAB-7-158
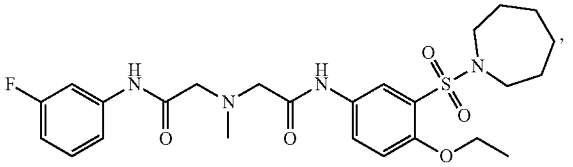
JAB-7-160
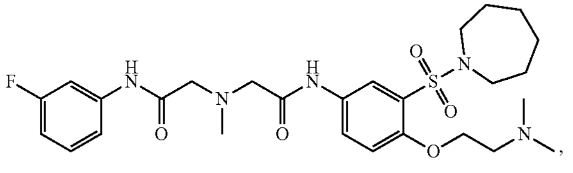
JAB-7-181
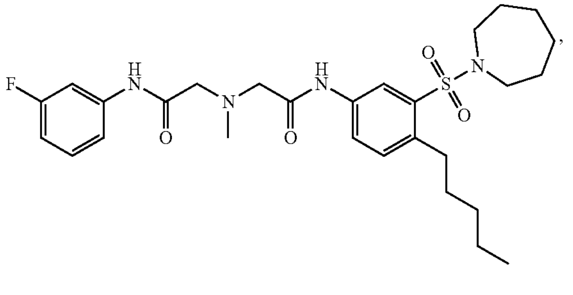

-continued
JAB-8-54
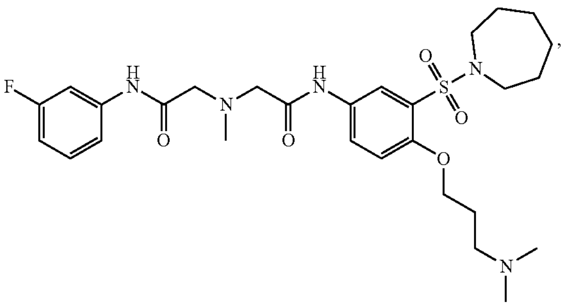
JAB-8-55
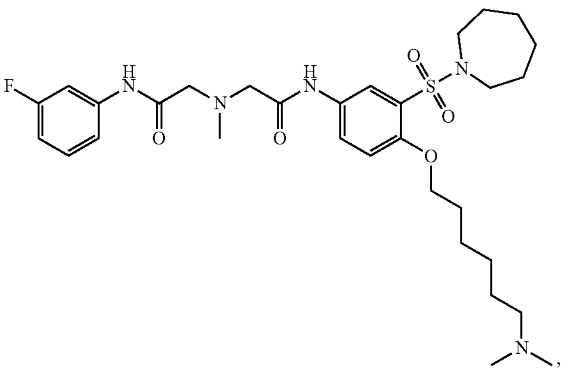
JAB-8-60
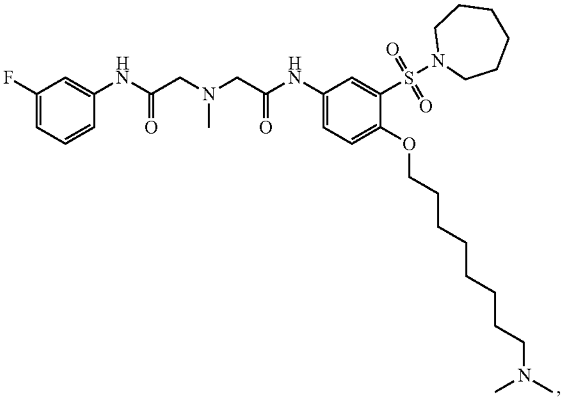
JAB-8-63
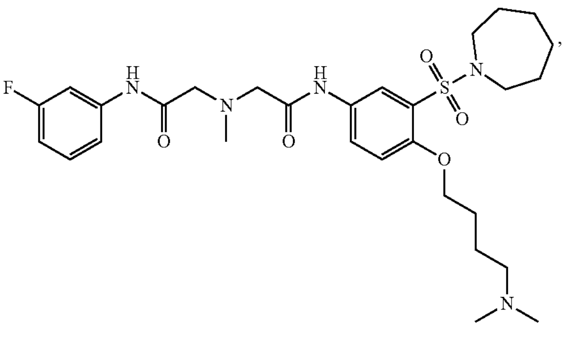
-continued
JAB-8-66
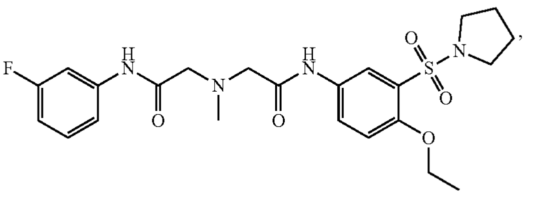
and
JAB-8-68
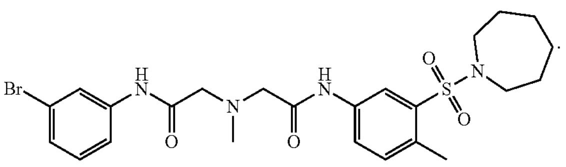
2. The compound of claim 1 selected from the group consisting of
JAB-6-1
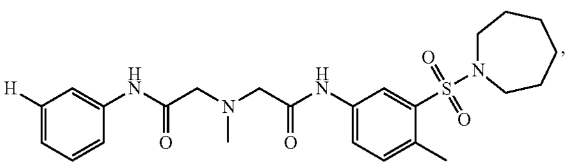
JAB-6-4
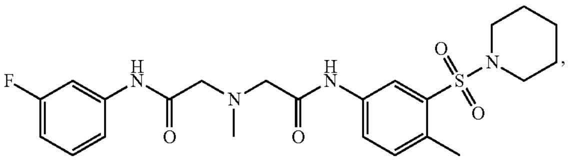
JAB-6-5
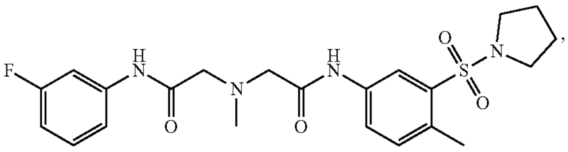
JAB-6-10
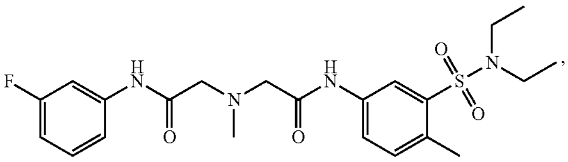
JAB-6-11
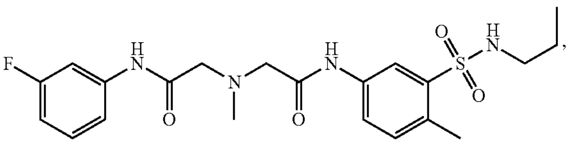
JAB-6-18
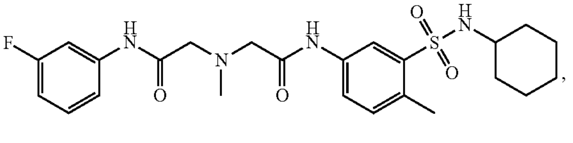

-continued
JAB-6-41
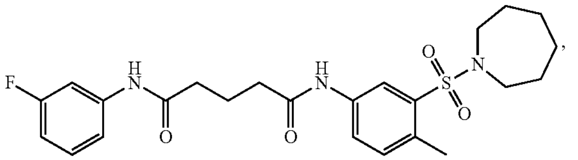
JAB-6-46
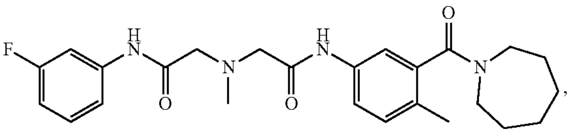
JAB-6-48
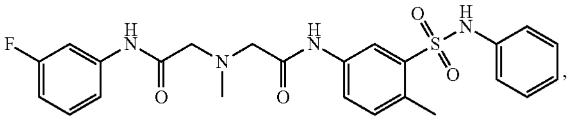
JAB-6-50
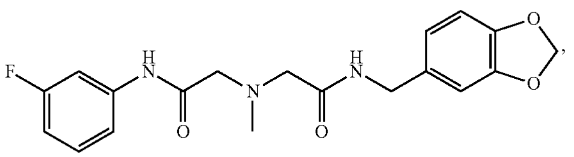
JAB-6-144
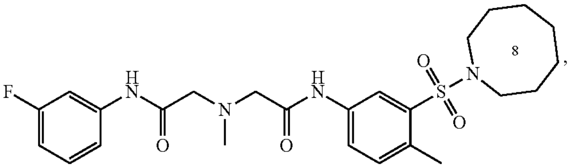
JAB-6-149
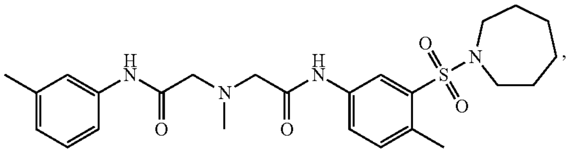
JAB-6-150
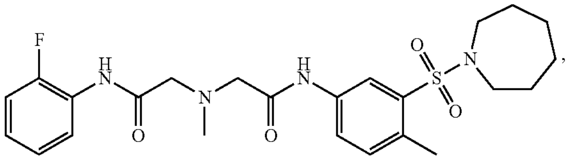
JAB-6-151
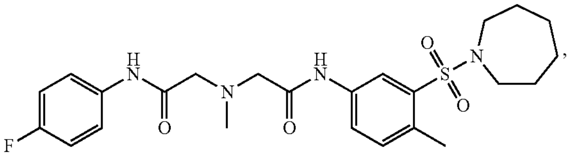
JAB-6-152
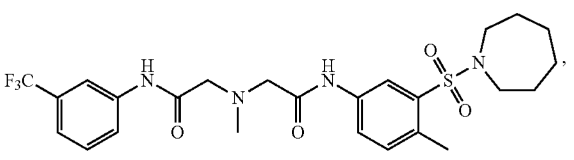
-continued
JAB-6-153
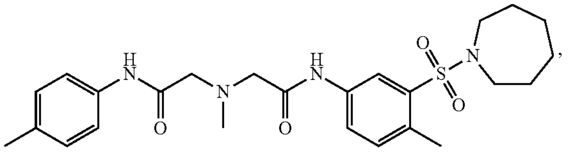
JAB-6-159
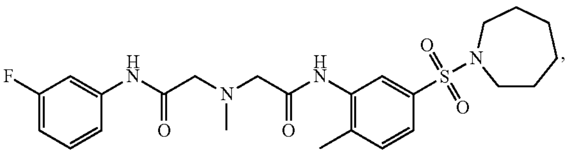
JAB-6-162
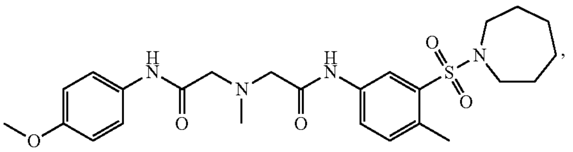
JAB-6-163
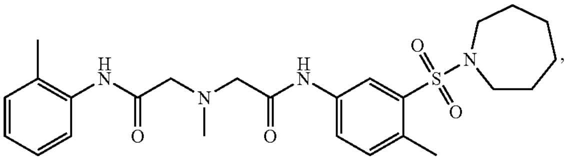
AB-6-164
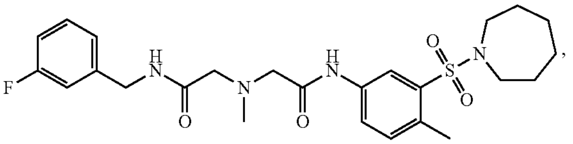
JAB-6-165
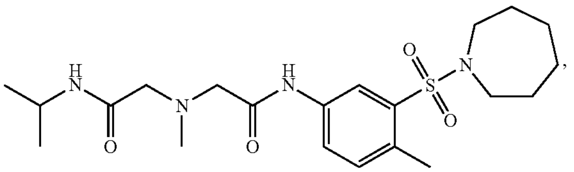
JAB-6-166
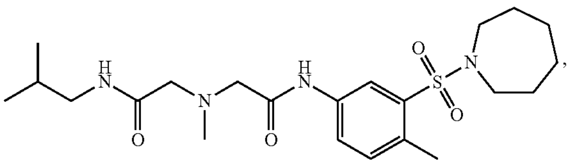
JAB-6-175
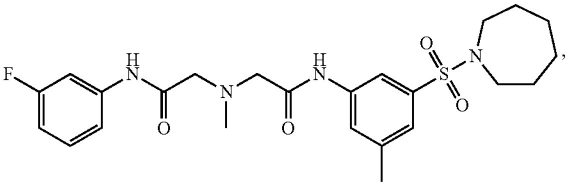

-continued
JAB-6-176
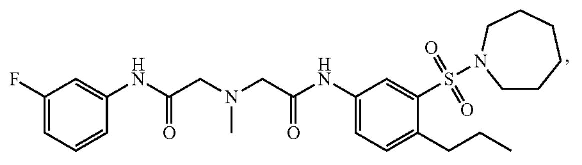
JAB-7-158
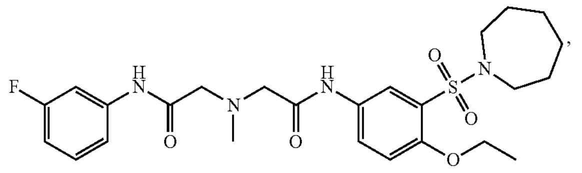
JAB-7-160
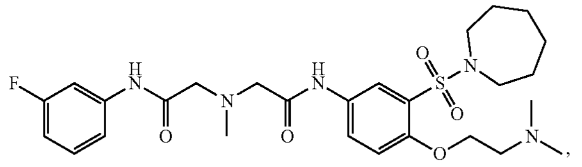
JAB-7-181
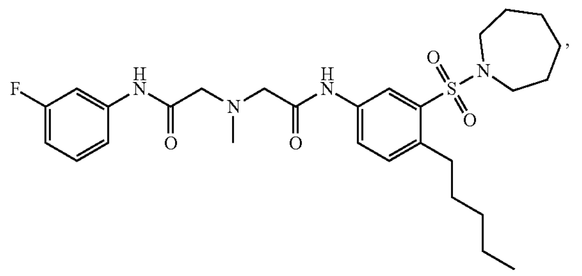
JAB-8-54
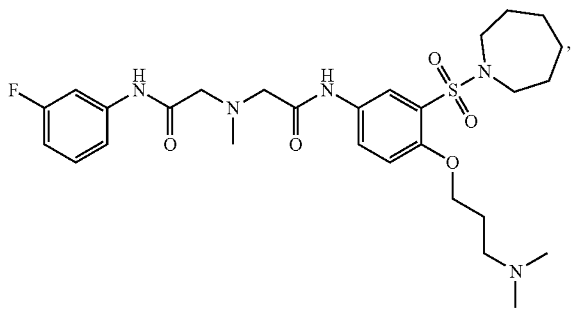
JAB-8-55
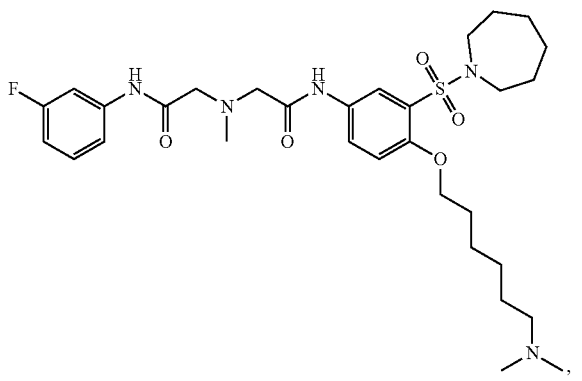
-continued
JAB-8-60
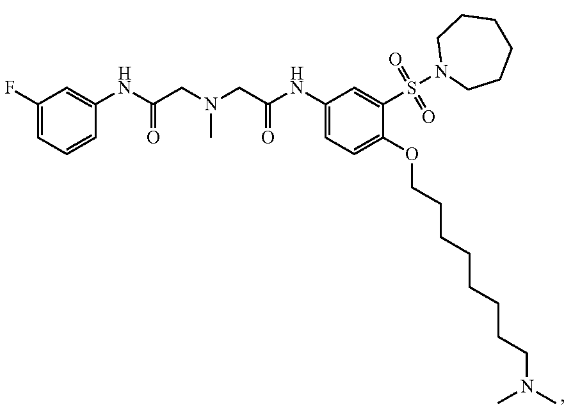
JAB-8-63
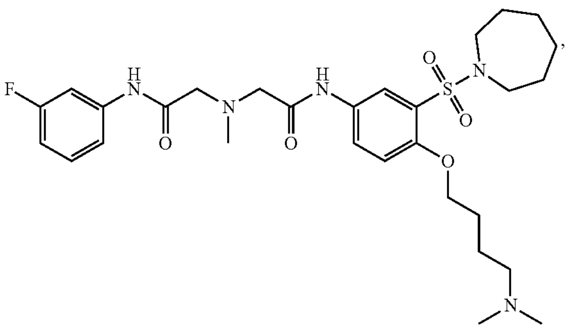
JAB-8-66
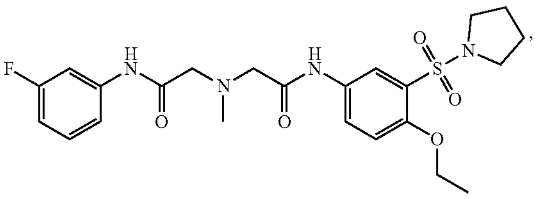 and
JAB-8-68
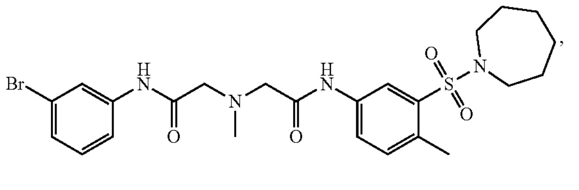
3. The compound of claim 1, selected from the group consisting of
JAB-6-5
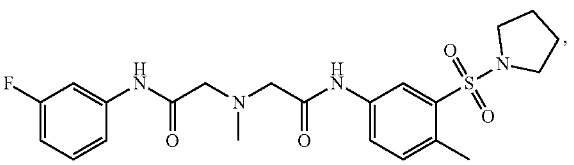

-continued
JAB-6-151
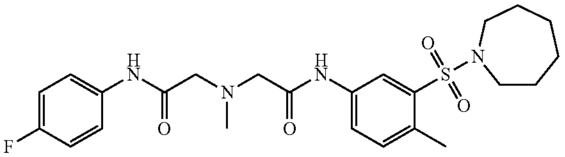,
JAB-6-152
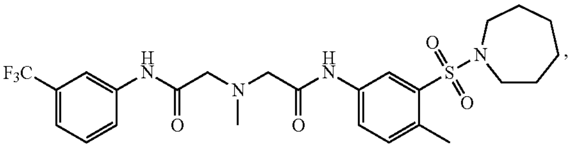,
JAB-6-153
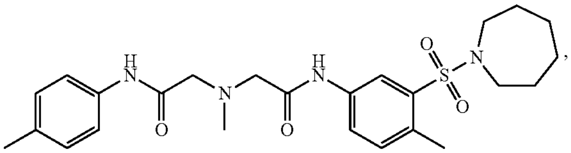,
JAB-6-156
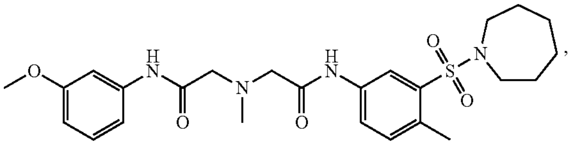,
JAB-6-159
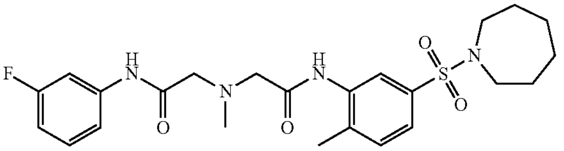,
JAB-6-162
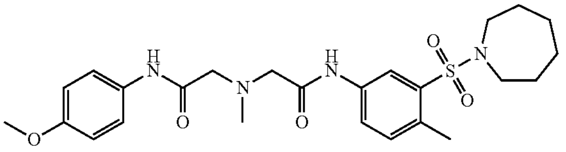,
JAB-6-163
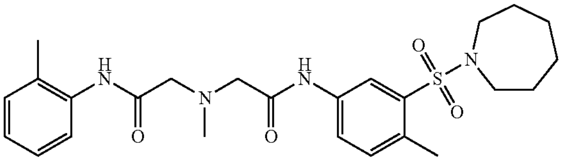,
JAB-6-164
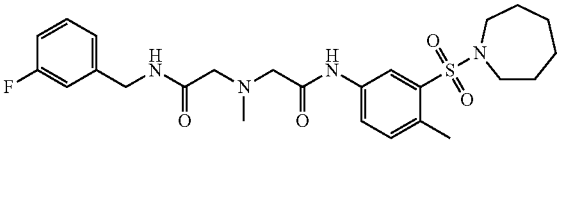,
-continued
JAB-6-165
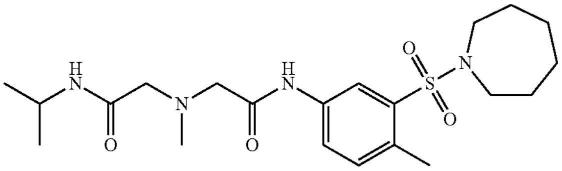,
JAB-6-166
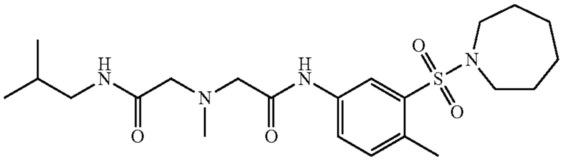,
JAB-6-175
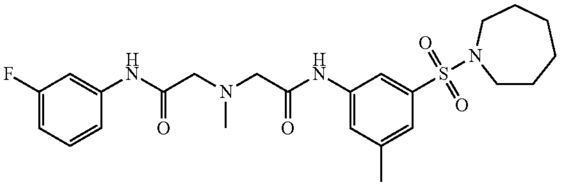,
JAB-6-176
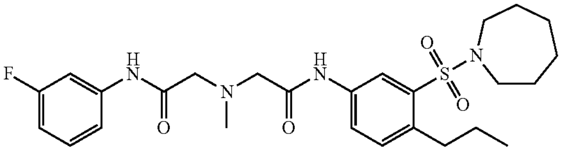,
JAB-7-158
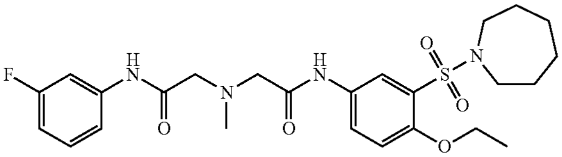,
JAB-7-160
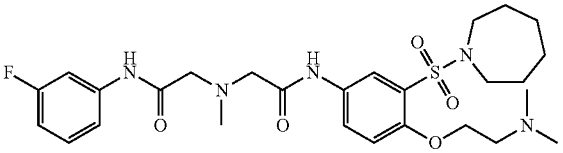,
and
JAB-8-60
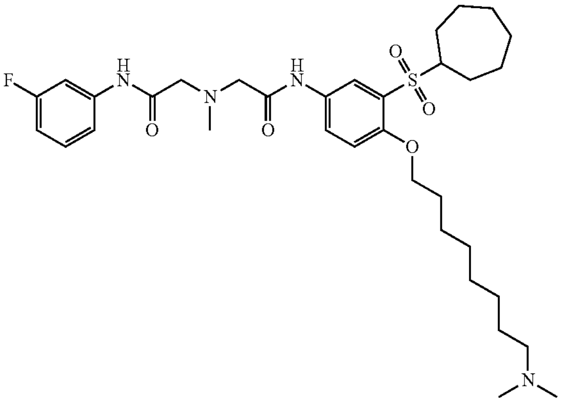.

4. The compound of claim 1, selected from the group consisting of
JAB-6-5
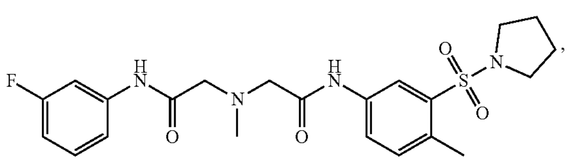
JAB-6-151
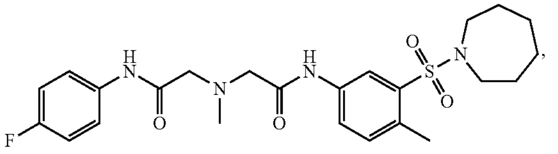
JAB-6-152
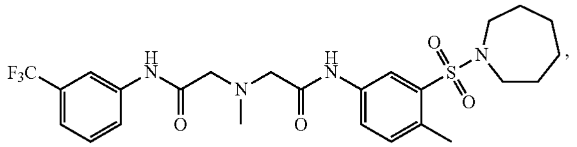
JAB-6-153
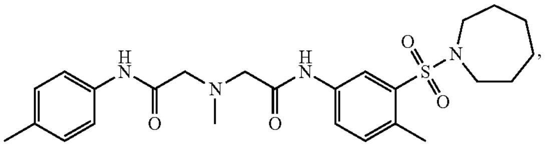
JAB-6-159
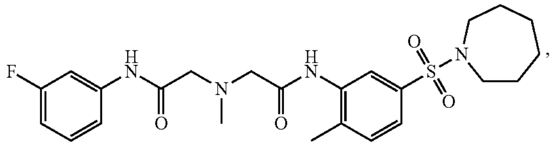
JAB-6-162
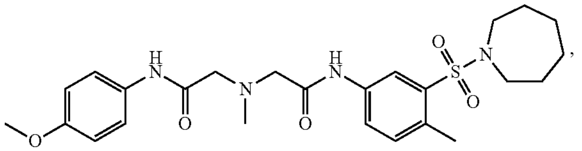
JAB-6-163
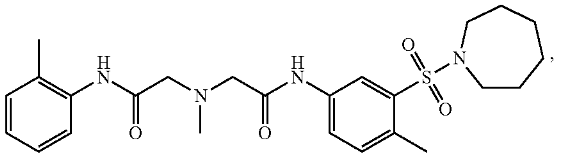
JAB-6-164
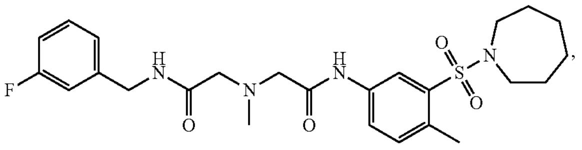
-continued
JAB-6-165
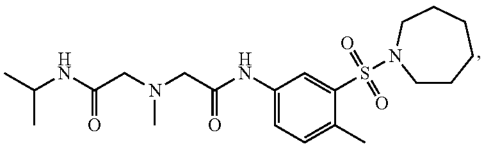
JAB-6-166
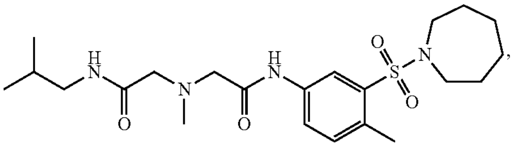
JAB-6-175
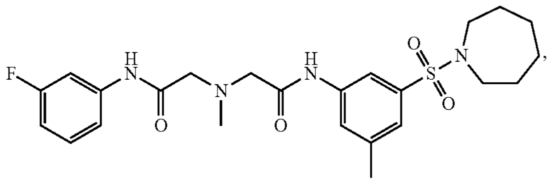
JAB-6-176
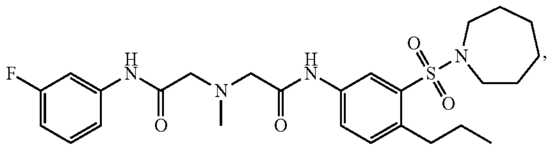
JAB-7-158
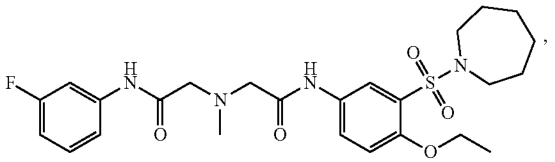
JAB-7-160
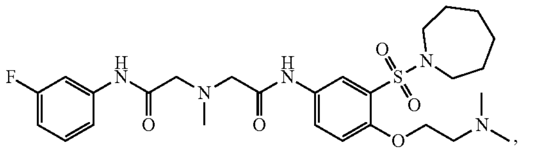
and
JAB-8-60
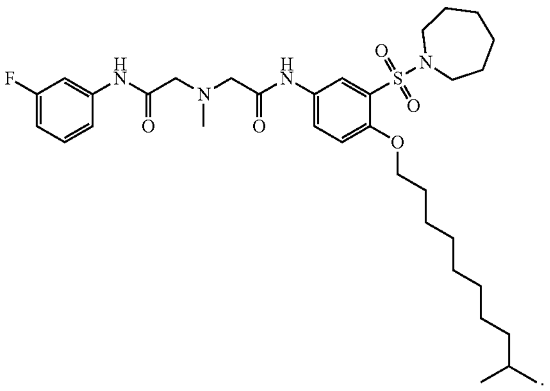
5. A composition comprising the compound of claim 1.
6. A pharmaceutical composition comprising the compound of claim 1.

7. A pharmaceutical composition comprising the compound of claim 1 and a pharmaceutically acceptable carrier.

8. A method of treating a disease associated with activating mutations in RAS, or treating a disease treatable by a reduction in RAS activity, comprising administering to a patient a compound selected from the group consisting of

JAB-6-1

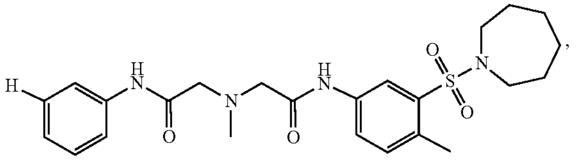

JAB-6-4

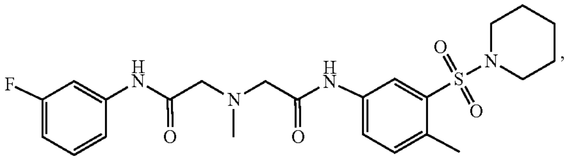

JAB-6-5

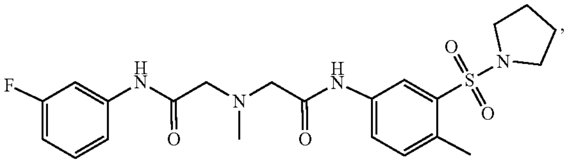

JAB-6-10

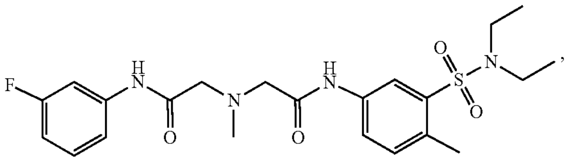

JAB-6-11

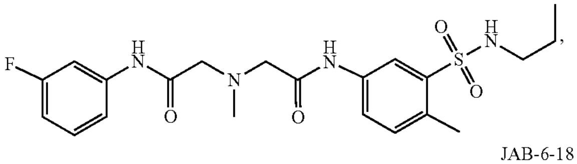

JAB-6-18

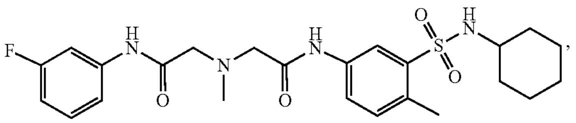

JAB-6-26

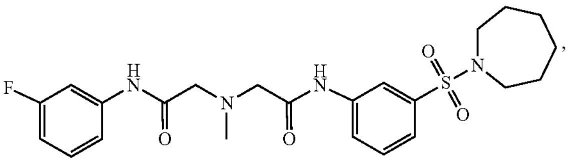

JAB-6-41

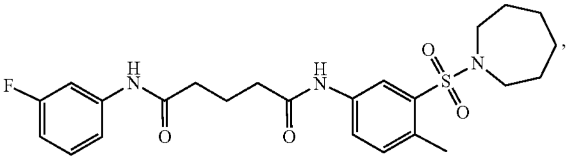

-continued

JAB-6-46

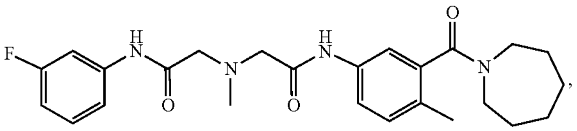

JAB-6-48

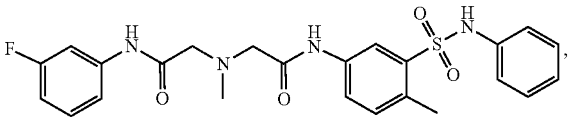

JAB-6-49

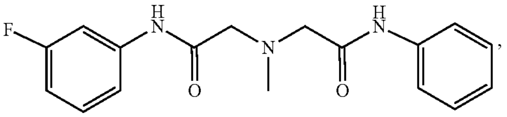

JAB-6-50

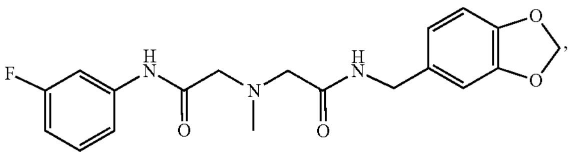

JAB-6-51

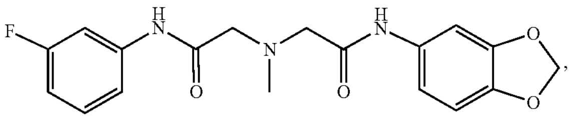

JAB-6-144

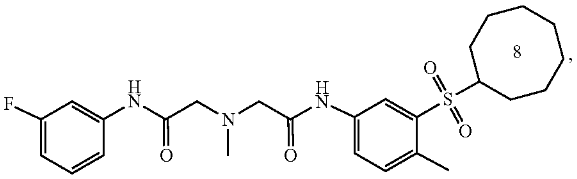

JAB-6-149

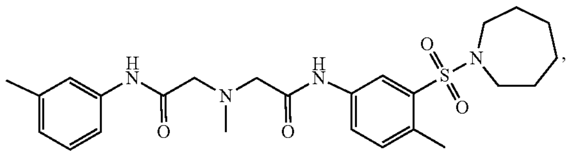

JAB-6-150

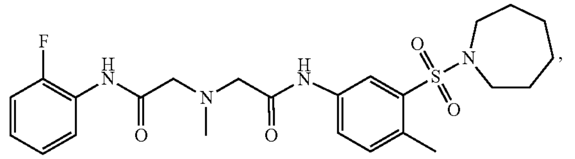

JAB-6-151

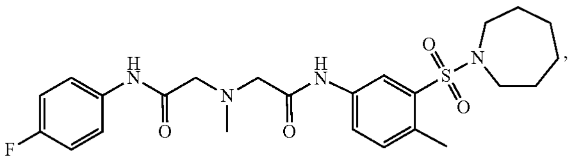

-continued
JAB-6-152
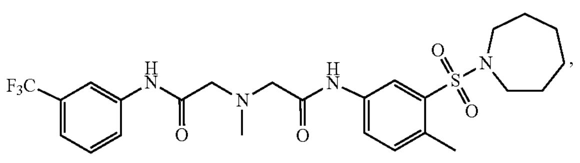
JAB-6-153
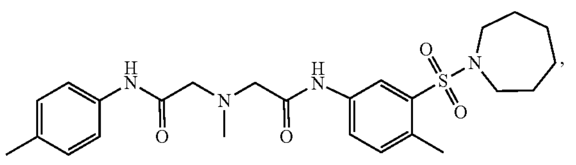
JAB-6-156
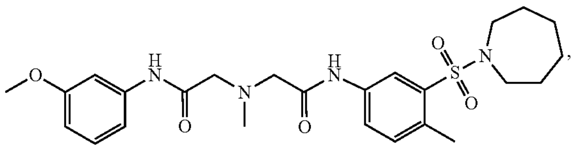
JAB-6-159
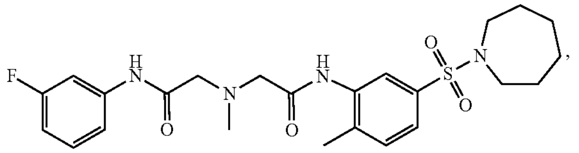
JAB-6-162
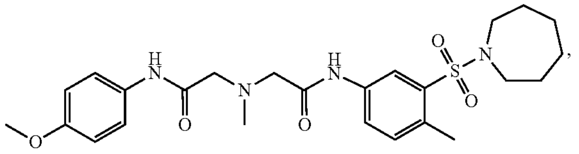
JAB-6-163
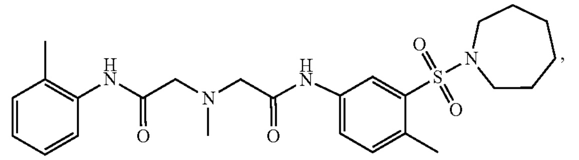
JAB-6-164
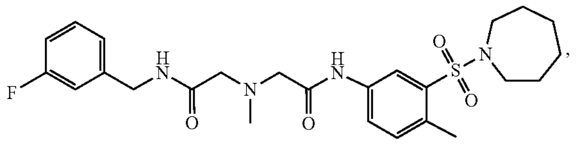
JAB-6-165
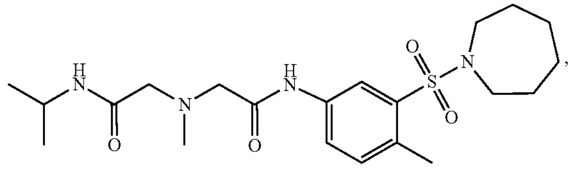
-continued
JAB-6-166
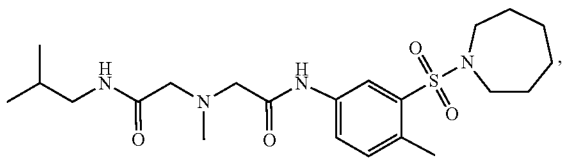
JAB-6-175
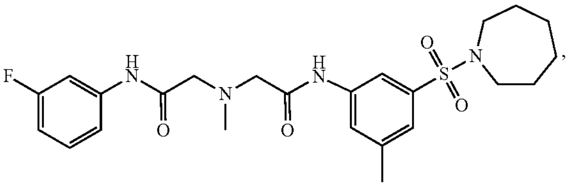
JAB-6-176
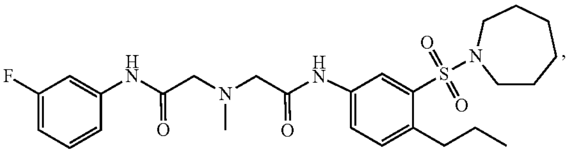
JAB-7-158
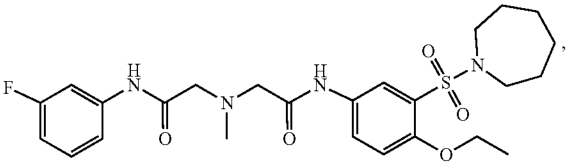
JAB-7-160
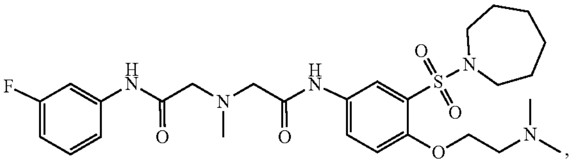
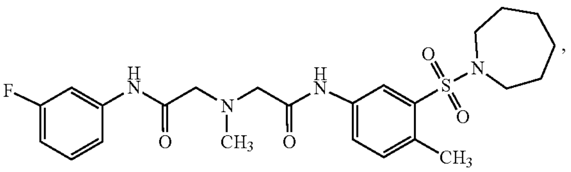
JAB-7-181
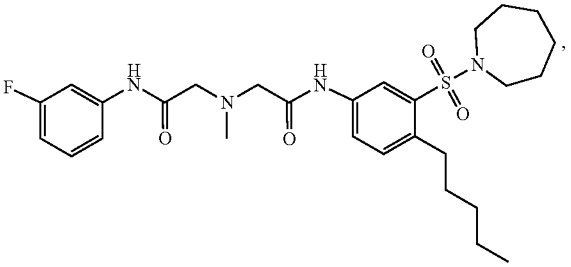

-continued

JAB-8-54

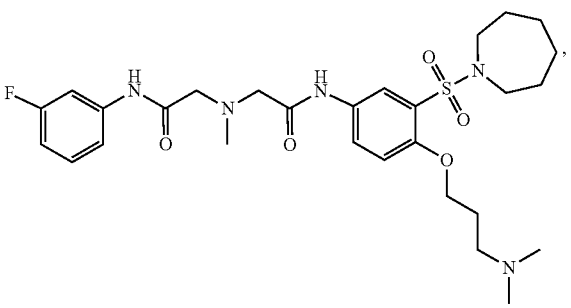

JAB-8-55

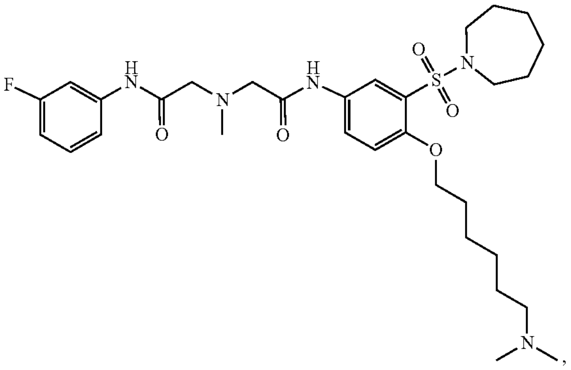

JAB-8-60

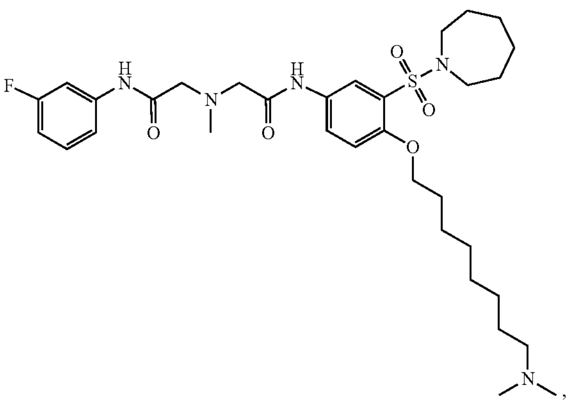

JAB-8-63

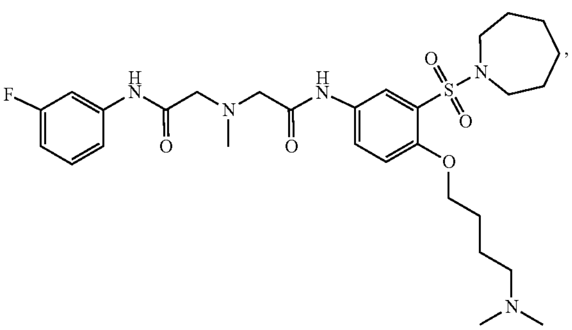

-continued

JAB-8-66

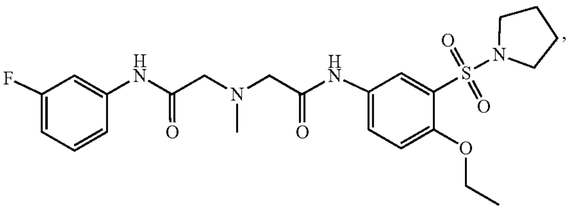

and

JAB-8-68

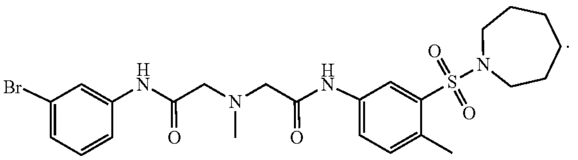

9. The method of claim 8, wherein the patient is in need of treatment.

10. The method of claim 8, wherein the patient is human.

11. The method of claim 8, wherein in the disease is a tumor or cancer.

12. The method of claim 8, wherein in the disease is a tumor or cancer and the tumor or cancer is pancreatic ductal adenocarcinoma, colorectal adenocarcinoma, multiple myeloma, lung adenocarcinoma, skin cutaneous melanoma, uterine corpus endometrioidcarcinoma, uterine carcinosarcoma, thyroid carcinoma, acute myeloid leukemia, bladder urothelial carcinoma, gastric adenocarcinoma, cervical adenocarcinoma, head and neck squamous cell carcinoma, melanoma, lymphoma, plasmocytoma, sarcoma, glioma, thymoma, leukemia, breast cancer, prostate cancer, colon cancer, liver cancer, esophageal cancer, brain cancer, lung cancer, pancreatic cancer, ovary cancer, endometrial cancer, bladder cancer, kidney cancer, cervical cancer, hepatoma, ovary cancer, cervix cancer, skin cancer, colorectal cancer, thyroid cancer, seminoma, melanoma, myeloid cancers, lymphoid disorders, MPNST, medulloblastoma, AML, or metastatic cancers.

13. The method of claim 8, wherein in the disease is a tumor or cancer and the tumor or cancer is pancreatic ductal adenocarcinoma, colorectal adenocarcinoma, multiple myeloma, lung adenocarcinoma, skin cutaneous melanoma, uterine corpus endometrioidcarcinoma, uterine carcinosarcoma, thyroid carcinoma, acute myeloid leukemia, bladder urothelial carcinoma, gastric adenocarcinoma, cervical adenocarcinoma, head and neck squamous cell carcinoma, lung cancer, MPNST, medulloblastoma, AML, or pancreatic cancer.

14. The method of claim 8, wherein in the disease is a tumor or cancer and the tumor or cancer is pancreatic ductal adenocarcinoma, colorectal adenocarcinoma, multiple myeloma, lung adenocarcinoma, skin cutaneous melanoma, uterine corpus endometrioidcarcinoma, lung cancer, MPNST, medulloblastoma, AML, or pancreatic cancer.

15. The method of claim 8, wherein in the disease is a tumor or cancer and the tumor or cancer is ovarian cancer, melanoma, kidney cancer, MPNST, medulloblastoma, AML, lung cancer, or pancreatic cancer.

16. The method of claim 8, further comprising administering at least one member selected from the group consisting of pembrolizumab, nivolumab, AS1411, and AS1411 conjugated to gold nanoparticles.

17. The method of claim 8, wherein the administering is intravenous, intradermal, subcutaneous, oral, inhalation, transdermal, transmucosal, or rectal administration.

18. The method of claim 8, wherein the administering is oral administration.

19. The method of claim 8, wherein the compound is the compound from claim 1.

20. The method of claim 8, wherein the compound is the compound from claim 3.

* * * * *